US010575751B2

United States Patent
Abeyratne et al.

(10) Patent No.: US 10,575,751 B2
(45) Date of Patent: Mar. 3, 2020

(54) METHOD AND APPARATUS FOR DETERMINING SLEEP STATES

(75) Inventors: Udantha Abeyratne, Forest Lake (AU); Vinayak Swarnkar, Toowong (AU)

(73) Assignee: THE UNIVERSITY OF QUEENSLAND, St. Lucia, Brisbane (AU)

( * ) Notice: Subject to any disclaimer, the term of this patent is extended or adjusted under 35 U.S.C. 154(b) by 637 days.

(21) Appl. No.: 13/131,712

(22) PCT Filed: Nov. 27, 2009

(86) PCT No.: PCT/AU2009/001554
§ 371 (c)(1),
(2), (4) Date: Aug. 15, 2011

(87) PCT Pub. No.: WO2010/060153
PCT Pub. Date: Jun. 3, 2010

(65) Prior Publication Data
US 2011/0301487 A1    Dec. 8, 2011

(30) Foreign Application Priority Data
Nov. 28, 2008 (AU) ................................ 2008906167

(51) Int. Cl.
*A61B 5/048* (2006.01)
*A61B 5/0476* (2006.01)
*A61B 5/00* (2006.01)

(52) U.S. Cl.
CPC ............ *A61B 5/048* (2013.01); *A61B 5/0476* (2013.01); *A61B 5/4809* (2013.01); *A61B 5/4812* (2013.01)

(58) Field of Classification Search
CPC . A61B 5/0476; A61B 5/04012; A61B 5/4821; A61B 5/0006; A61B 5/4812; A61B 5/4809; A61M 2230/10
(Continued)

(56) References Cited

U.S. PATENT DOCUMENTS

2001/0031930 A1* 10/2001 Roizen ..................... A61B 5/18
600/544
2003/0167019 A1* 9/2003 Viertio-Oja et al. ......... 600/544
(Continued)

FOREIGN PATENT DOCUMENTS

EP    1859736       11/2007
EP    1859736 A1 *  11/2007

OTHER PUBLICATIONS

Akgul, Characterization of Sleep Spindles Using Higher Order Statistics and Spectra, IEEE Transactions of Biomedical Engineering, vol. 47, No. 8, Aug. 2000, pp. 997-1009.*
(Continued)

*Primary Examiner* — Puya Agahi
(74) *Attorney, Agent, or Firm* — Nixon & Vanderhye PC

(57) ABSTRACT

An apparatus is provided for detecting Macro Sleep Architecture states of a subject such as WAKE, NREM and REM sleep from a subject's EEG. The apparatus includes an EEG digital signal assembly of modules arranged to convert analogue EEG signals into digital EEG signals. A bispectrum assembly is responsive to the EEG digital signal assembly and converts the digital EEG signals into signals representing corresponding bispectrum values. A bispectrum time series assembly, in electrical communication with an output side of the bispectrum assembly, generates at least one bispectrum time series for a predetermined frequency. A macro-sleep architecture (MSA) assembly is responsive to the bispectrum time series assembly and is arranged to produce classification signals indicating classification of segments of the EEG signals into macro-sleep states of the subject.

11 Claims, 21 Drawing Sheets

(58) Field of Classification Search
USPC .......................................................... 600/544
See application file for complete search history.

(56) References Cited

U.S. PATENT DOCUMENTS

| | | | |
|---|---|---|---|
| 2004/0193068 A1* | 9/2004 | Burton et al. | ................ 600/544 |
| 2005/0043652 A1* | 2/2005 | Lovett | ..................... A61B 5/00 |
| | | | 600/595 |
| 2007/0016095 A1 | 1/2007 | Low et al. | |
| 2007/0270706 A1* | 11/2007 | Merilainen et al. | .......... 600/544 |

OTHER PUBLICATIONS

Ning et al., Bispectral Analysis of the Rat EEG During Various Vigilance States, IEEE Transactions on Biomedical Engineering, vol. 36, No. 4, pp. 497-499, Apr. 1989.*

Ng et al., Bispectral Analysis of Snore Signals for Obstructive Sleep Apnea Detection, Proceeding of the 29th Annual International, Conference of the IEEE EMBS, Aug. 23-26, 2007, pp. 6195-6198.*

International Search Report for PCT/AU2009/001554, dated Feb. 11, 2010.

Written Opinion of the International Searching Authority for PCT/AU2009/001554, dated Feb. 11, 2010.

Akgul, T. et al., "Characterization of Sleep Spindless Using Higher Order Statistics and Spectra", IEEE Transaction on Biomedical Engineering, vol. 47(8), (Aug. 2000), pp. 997-1009.

"How Does the BIS Monitor Work?" retrieved Aug. 29, 2016, 1 page. https://www.scribd.com/doc/30788270/How-the-BIS-Monitor-Works.

\* cited by examiner

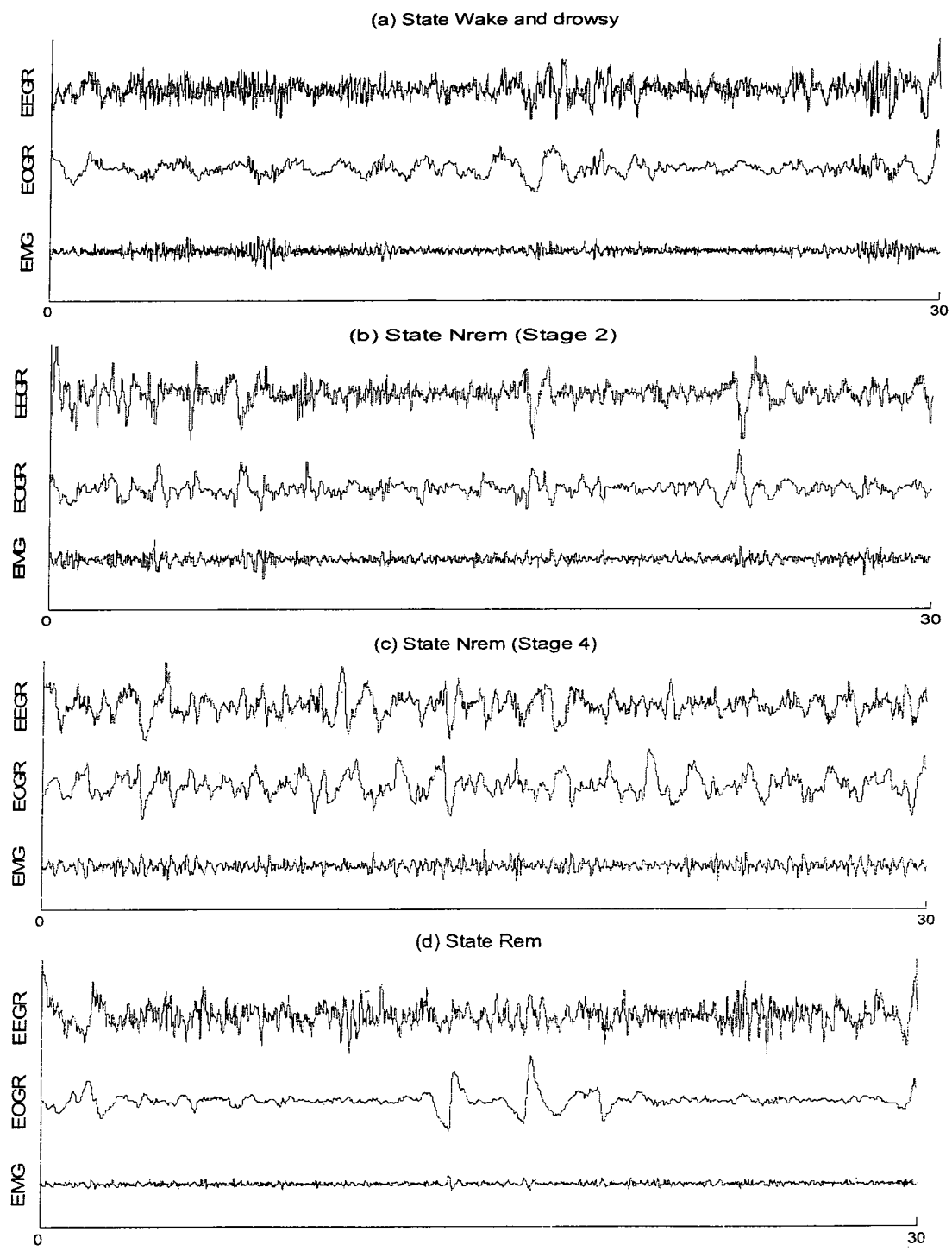

Figure 1: EEG, EOG and EMG activity during different sleep states. (a) State wake and drowsy, EEG activity of 5-8 Hz, slow eye movement and voluntary EMG activity. (b) State Nrem in state 2, EEG showing features such as k-complex and spindles. (c) State Nrem in stage 3 and 4. EEG showing high delta activity (1-3 Hz). (d) State Rem. EEG activity between theta and alpha range. Intermittent eye movement and suppressed EMG activity.

Figure 1

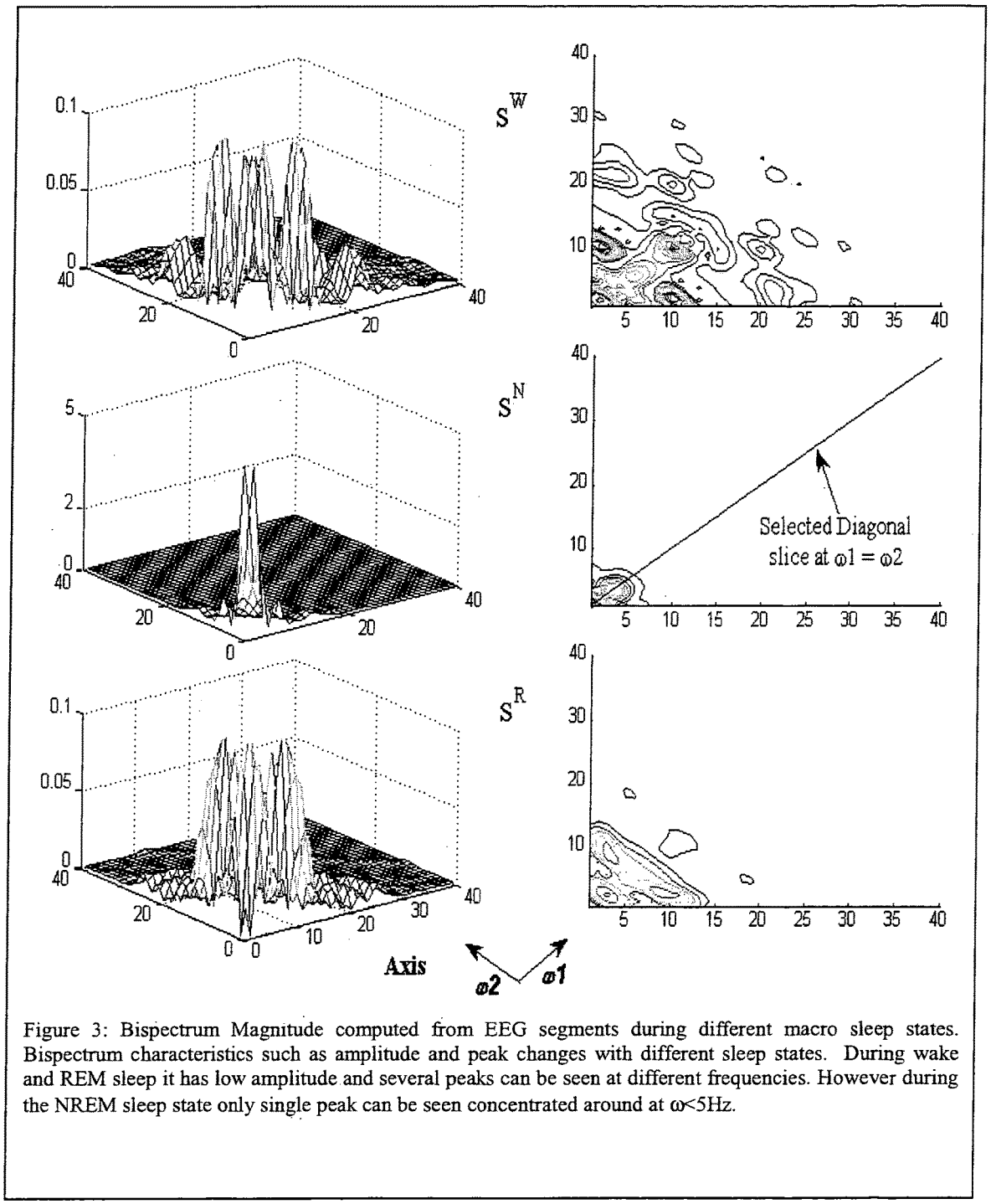

Figure 3: Bispectrum Magnitude computed from EEG segments during different macro sleep states. Bispectrum characteristics such as amplitude and peak changes with different sleep states. During wake and REM sleep it has low amplitude and several peaks can be seen at different frequencies. However during the NREM sleep state only single peak can be seen concentrated around at ω<5Hz.

Figure 3

Figure 11: Scattered plot showing the correlation between the MSA parameters (TST, SE, RSL, %$S^W$ %$S^N$ and %$S^R$) computed from TSSS and HESS.

Figure 12: Altman Bland Plot comparing MSA parameters; TST, SE, RSL, %$S^W$, %$S^N$ and %$S^R$ computed from TSSS and HESS.

METHOD AND APPARATUS FOR DETERMINING SLEEP STATES

This application is a National Phase Application of International Application No. PCT/AU2009/001554, filed on Nov. 27, 2009, which designated the U.S., and claims priority to Australia Application No. 2008906167, filed on Nov. 28, 2008, the entire contents of each of which are hereby incorporated by reference.

FIELD OF THE INVENTION

The present invention is concerned with a method and apparatus for automatically determining states of sleep of a subject. Embodiments of the invention find particular application in aiding the diagnosis of sleep disorders and assessing daytime sleepiness.

BACKGROUND

The reference to the prior art in the following discussion is not to be taken as any representation or admission that such art forms part of the common general knowledge. The disclosures of each of the publications referred to herein are hereby incorporated by reference in their entireties and for all purposes.

Obstructive sleep apnea hypopnea syndrome (OSAHS) is a serious sleep disorder with high prevalence among the population [1, 2]. In the USA, about 24% of men and 9% of women fall within Medicare guidelines [1] for treatment. In Singapore 15% of the total population is at risk [3]. Over 1.2 million Australians experience sleep disorders costing the country $10.3 billion (in 2004) [4]; OSAHS is the commonest disorder (66% of the total).

OSAHS is characterized by breathing interruption during sleep. Full closure of the airways is known as obstructive Apnea, and a partial closure is defined as obstructive Hypopnea (See Appendix A for technical definitions). The common symptoms of OSAHS are excessive daytime sleepiness and intermittent snoring [5, 6].

OSAHS is a major risk factor for downstream complications such as stroke, diabetes and cardiovascular disease [6, 7]. It is also known to be associated with cognitive deficiencies, low IQ in children, fatigue and accidents. It is responsible [7] for 11,000-43,000 traffic accidents per year in NSW. Untreated patients are known to utilize twice the national health resources prior to diagnosis [8]. OSAHS is treatable. If diagnosed early, its devastating secondary complications can be thwarted. However, over 90% individuals with OSAHS are estimated to be undiagnosed at present [2].

The standard test for OSAHS diagnosis is Polysomnography (PSG) [9]. PSG is a technique to monitor multiple neuro-physiological and cardio respiratory signals, over the course of night. It requires a full-night sleep-laboratory stay in a specifically equipped sleep-suite, connected to over 15 channels of measurements. The 6-8 hours of sleep data is then subjected to a complex and time-consuming manual process (Sleep Scoring) to identify events of Apnea/Hypopnea and a type of sleep a disturbance known as EEG-arousals (EEGA). The outcomes of PSG test are summary measures of OSAHS severity such as the Respiratory Disturbance Index (RDI) and the EEG Arousal index (ArI) etc (please see appendix B for details).

EEG in the Diagnosis of Sleep Disorders
Sleep Scoring and Macro-Sleep-Architecture Sleep is essentially a neuropsychological phenomenon; EEG still remains the cheapest and the most portable technique for the functional imaging of the brain during sleep. It is also the technique with the highest temporal resolution available. In the current practice of PSG Scoring, EEG is regarded as an indispensable signal when a definitive diagnosis is desired. Thus, in-facility diagnostic PSG tests always include EEG. Electromyography (EMG) and Electrooculography (EOG) signals are also needed for the correct EEG-centred interpretation of sleep states.

In diagnostic PSG tests EEGs are essential for the following tasks:

(i) to define EEG-arousals and identify sleep fragmentation. EEG-arousals are also used as one parameter in defining Hypopneas (see Appendix A).
  (ii) to score the Macro Sleep Architecture (MSA) of sleep. It is a process in which sleep is classified into three macro states: (1) Wake State ($S^W$), (2) Rapid Eye Movement (REM) Sleep State ($S^R$), and (3) Non-REM Sleep State ($S^N$). The MSA is extremely important in the diagnosis of OSAH. In addition, Sleep MSA may be used in the diagnosis/monitoring of a range of sleep disorders including Narcolepsy, Insomnia, Sudden Infant Death Syndrome and Depression etc.
  Some important uses of MSA in PSG includes:
  (a) Estimating the Total Sleep Time, TST, which is needed for the computation of the RDI index. The TST is also useful as a summary indicator of the quality of sleep during a PSG test. Note that the TST, which is defined using EEG, can be significantly different from the Total Time in Bed (TTB) measured with a clock.
  (b) Estimating clinically important descriptors of sleep such as the Sleep Efficiency (SE), Sleep Latency (SL), REM Latency (RSL), the total time spent in REM, and the percentage of time spent in REM.
  (c) Expressing most of the clinically relevant sleep parameters separately for REM and NREM sleep, before providing an overall number. Some Examples are: the Arousal Index in REM sleep, The Arousal Index in NREM sleep, RDI in REM sleep and RDI index in NREM sleep. The reason behind this is that the REM/NREM classification provides fundamental information about sleep and its diagnostic characteristics.

An EEG may be broadly divided into four major frequency bands [10], Delta (δ, 0.1-4 Hz), Theta (θ, 4.1-8 Hz), Alpha (α, 8.1-12 Hz), and Beta (β, >12.1 Hz). FIG. 1 shows the EEG activity at different states, (a) awake drowsy state, (b) light sleep (NREM sleep Stage 1 and Stage 2), (c) deep sleep (NREM sleep Stage 3 and Stage 4) and (d) REM sleep. These frequency bands are heavily used in sleep scoring.

The scoring of MSA is done manually using the rules laid down by Rechtschaffen and Kales (R&K, 1968) (see appendix C for a summary) [11]. Manual scoring relies on visual extraction of specific features in two EEG channels (usually C3-A2 and C4-A1 of the International 10/20 system), two channels each of EMG and EOG. Thus, six channels of electrophysiological data have to be visually interpreted, simultaneously taking care of difficulties such as measurement artifacts.

This process is time consuming (typically 1-2 hours per patient), costly (hundred of dollar per recording) and prone to inter and intra scorer variability [12-15]. The scorers from different laboratories tend to agree less than scorers from the same laboratories, due to differences in interpretation and subjective implementations. For example, the mean epoch by epoch agreement between the scorers from three sleep laboratories in the USA for healthy subjects is 76% (range 65-85%) which decreases to 71% (range 65-78%) in the OSAHS cases [16]. A similar result (76.8%) has been reported by European laboratories based on a large database of 196 recordings from 98 patients [13].

The accurate computation of sleep parameters such as the RDI, ArI and REM Latency is important for the clinical diagnosis of a range of sleep disorders. Thus, the final diagnostic accuracy heavily depends on the precise scoring of MSA. However, due to the subjectivity associated with the scoring process there exists a significant variability in the PSG results between the technicians of the same laboratory and across the different sleep laboratories [14, 15]. For example, [12] reported that a patient can get two different diagnoses in two different laboratories which might range from as low as RDI=4.9 to as high as RDI=79.

In order to overcome the problems associated with manual scoring and cater to the ever increasing demand for PSG testing, several researchers have proposed automatic sleep scoring systems [17-22]. After publication of R&K's rules in 1968, several authors tried to automate them and achieved various degrees of agreement with human scorers. With the advancement in digital signal processing techniques, several other used frequency spectral analysis [22], neural network analysis [18, 20], multidimensional scaling and wavelets techniques or expert system approaches [21] to develop automatic sleep staging systems. However, a reliable and accurate method with sufficient precision suitable for in-facility PSG as well as other take-home OSAHS screening devices does not exist yet. Despite the inherent subjective nature, human scoring is still considered the golden method of MSA scoring. Existing methods for automatic MSA scoring have the following shortcomings:

1. The R&K rules depend on visual features in sleep EEG and were originally proposed specifically for manual scoring. Most of the automated techniques try to implement R&K rules and depend on morphological features like k-complexes, vertex-waves and spindles. These characteristics are severely altered in disease states such as OSAHS [6, 10, 23, 24]. Consequently their performances decreases in OSAHS [19, 25]. In addition, the detection of visual features is a highly subjective process.
2. The agreement between automatic and human classifications is smaller than the agreement between human scorers [25]. This result is to be expected because the R&K criteria are based on visual features and humans are better than machines in visual pattern recognition.
3. The differentiation of REM/NREM/WAKE is critical in OSAHS diagnosis. However, automated methods had difficulties in distinguishing wake state from Stage 1 of NREM sleep and REM sleep.
4. Automated scoring techniques currently available in PSG equipment need expert human intervention for manually editing the outcomes, and thus are not truly automated systems [25]. The human intervention makes them subjective and time consuming.
5. Existing methods have not been tested under disease conditions such as OSAHS, Periodic Leg Movement Syndrome (PLMS) or upper airway respiratory syndrome (UARS), where sleep is corrupted with frequent EEG arousals, apnea events, and recording artifacts.
6. All existing techniques depend on recording multiple physiological signals, making them unsuitable for portable monitors used for OSAHS screening.

The AASM definition [26] of micro-sleep is: " . . . an episode lasting up to 30 seconds during which external stimuli are not perceived. The PSG suddenly shifts from waking characteristics to sleep". It is generally believed that micro-sleep is closely associated with excessive diurnal sleepiness. Excessive daytime sleepiness and spontaneous micro-sleep are two major consequences of OSAHS [27], contributing to motor vehicle and work related accidents. It is estimated to affect 12% of the adult population [27].

Clinically, sleepiness is commonly expressed by the measure Sleep Latency (SL), which is the length of time required to fall asleep. The common tests for measuring SL are Multiple Sleep Latency Test (MSLT) and Maintenance of Wakefulness Test (MWT), technical details for which are provided in Appendix E. In these tests SL is computed as the time from the start of recording to the sleep onset. To technically identify sleep onset, sleep technician have to simultaneously look at multiple signals. It is a tedious and a subjective process resulting in high inter-rater, as well as intra-rater, variability [12]. The SL also provides valuable information in the diagnosis of other widespread diseases such as insomnia.

Even though diurnal micro-sleep is an important phenomenon related to sleep disturbances, there is no objective system of measurements to detect micro-sleep or express its severity. In routine PSG tests targeted for OSAHS diagnosis, episodes of micro-sleeps are not scored.

It is an object of the present invention to provide a method and apparatus that addresses one or more of the various problems discussed above in relation to prior art methods for determining sleep-related parameters.

SUMMARY OF THE INVENTION

According to a first aspect of the present invention there is provided a method of determining sleep states from an EEG signal of a subject, the method comprising the steps of:
electronically processing the EEG signal to generate a third or higher order spectrum of said signal;
electronically processing said spectrum to produce at least one spectrum time series for a predetermined frequency; and
electronically processing said spectrum time series for compliance with predetermined criteria to tangibly classify segments of the EEG signal as corresponding to particular macro-sleep states of the subject.

In one embodiment the segments of the EEG signal are tangibly classified by indicating their classification on an electronic display for viewing by a user.

Preferably the step of electronically processing the spectrum to produce at least one spectrum time series produces a first spectrum time series and a second spectrum time series for corresponding first and second frequencies.

Preferably the spectrum comprises a bispectrum and the spectrum time series comprises a bispectrum time series.

The step of electronically processing said bispectrum time series for compliance with predetermined criteria will preferably include processing the first bispectrum time series to classify a corresponding one of said segments as Wake or Sleep.

In a preferred embodiment the method involves a step of electronically processing the second bispectrum slice time series of said segment classified as Sleep to further classify said segment as NREM or REM sleep.

Preferably the step of electronically processing the bispectrum to produce at least one bispectrum time series produces a first bispectrum time series and a second bispectrum time series for corresponding first and second frequencies.

The step of electronically processing said bispectrum time series against predetermined criteria will preferably include processing the first bispectrum time series to classify a corresponding one of said segments as Wake or Sleep.

In a preferred embodiment the method involves a step of electronically processing the second bispectrum time series of said segment classified as Sleep to further classify said segment as NREM or REM sleep.

According to the preferred embodiment, the first frequency falls within a range of 1-8 Hz and the second frequency is greater than 9 Hz.

The method may include a step of electronically smoothing the second bispectrum time series prior to processing said second bispectrum time series against predetermined criteria.

The step of electronically processing the first bispectrum time series against predetermined criteria will preferably include comparing values of a segment of the first bispectrum time series to a threshold value computed from the first bispectrum time series.

Preferably the step of electronically processing the second bispectrum time series against predetermined criteria includes comparing values of a segment of the second bispectrum time series to a threshold value computed from the second bispectrum time series.

The method may include a step of indicating the particular macro-sleep states of the subject with an electronic display or another sensory signal modality such as a sound or tactile indication.

Preferably the step of generating a bispectrum by electronically processing the EEG signal comprises an indirect estimation method The indirect method may include applying a Fourier transform to cumulant values corresponding to the EEG signal.

Alternatively, the step of generating a bispectrum by electronically processing the EEG signal may comprise a direct estimation method.

The method may include a step of electronically processing the first bispectrum time series to produce an index indicating sleepiness of the subject.

Preferably the step of electronically processing the first bispectrum time series to produce said index comprises determining a fraction of time over a predetermined period that said series approaches a predetermined threshold value.

According to a further aspect of the present invention there is provided an apparatus for detecting sleep states of a subject including:
an EEG digital signal assembly of modules arranged to convert analogue EEG signals into digital EEG signals;
a spectrum assembly responsive to the EEG digital signal assembly and arranged to convert the digital EEG signals into signals representing spectrum values;
a spectrum time series assembly in electrical communication with an output side of the spectrum assembly and arranged to generate at least one spectrum time series for a predetermined frequency; and
a macro-sleep architecture (MSA) assembly responsive to the spectrum time series assembly and arranged to produce classification signals indicating classification of segments of the EEG signals into macro-sleep states of the subject.

Preferably the spectrum assembly is a bispectrum assembly that is arranged to convert the digital EEG signals into signals representing bispectrum values. Alternatively, other higher order spectrum assemblies might also be used, such as a trispectrum.

Preferably the spectrum time series assembly comprises a bispectrum time series assembly arranged to generate at least one bispectrum time series for a predetermined frequency.

In one embodiment, the macro-sleep architecture (MSA) assembly is responsive to the bispectrum time series assembly.

Preferably the EEG digital signal assembly includes:
one or more EEG electrode ports;
an analogue signal conditioning module in electrical communication with the EEG electrode ports;
an analogue to digital converter in electrical communication with the analogue signal conditioning module; and
a bandpass digital filter arranged to process output from the analogue to digital converter to produce the digital EEG signals.

Preferably the bispectrum assembly comprises:
a cumulant calculator;
a Fourier transform module responsive to the cumulant calculator to produce a signal representing values of a bispectogram; and
a bispectrum time series estimator arranged to produce at least one bispectrum time series signal representing values at a predetermined frequency of a slice of the bispectogram.

The MSA assembly preferably includes a comparator to determine if the value of the at least one bispectrum time series signal exceeds a predetermined value over a segment.

Preferably the apparatus includes a sleepiness index calculator responsive to the bispectrum time series estimator and arranged to generate a signal indicating sleepiness of the subject based on the bispectrum time series signal for the predetermined frequency falling within the EEG Delta band.

In a preferred embodiment the apparatus has a display to display a macro sleep status determined by the MSA.

The user interface may include a display in communication with the sleepiness index calculator to display the sleepiness index.

Preferably the apparatus is arranged as a driver sleep management system, wherein the sleepiness index calculator is incorporated into a sleepiness index alert unit, said alert unit controlling one or more of:
a driver intervention module for increasing the wakefulness of the driver;
a wireless communications module for communicating with a base station;
a vehicle control interface for appropriately and safely immobilising the vehicle; and
a data logger for recording sleepiness index values of the driver.

According to a further aspect of the present invention there is provided a media readable by machine, tangibly embodying a program of instructions executable by the machine to cause the machine to perform the previously described method to determine sleep states from an EEG of a subject.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings throughout as follows:

FIG. 1A is a graph of EEG, EOG and EMG activity of an awake and drowsy subject exhibiting EEG activity of 5-8 Hz, slow eye movement and voluntary EMG activity.

FIG. 1B is a graph of EEG, EOG and EMG activity of the subject in NREM stage 2 sleep with EEG showing features such as k-complex and spindles.

FIG. 1C is a graph of EEG, EOG and EMG activity of the subject in NREM stage 3 and 4 sleep, with EEG showing high delta activity (1-3 Hz).

FIG. 1D is a graph of EEG, EOG and EMG activity of the subject in REM sleep with EEG activity between theta and alpha range exhibiting intermittent eye movement and suppressed EMG activity.

FIG. 3 is a graph of bispectrum magnitude computed from EEG segments during different macro sleep states, namely Waking ($S^R$), NREM ($S^N$) and REM ($S^R$) from which it may be observed that during wake and REM sleep a low amplitude is present with several peaks to be seen at different frequencies, whereas during NREM sleep only a single peak can be seen concentrated around $\omega < 5$ Hz.

DETAILED DESCRIPTION OF PREFERRED EMBODIMENTS

Method

EEG Data Acquisition

Figure 2:
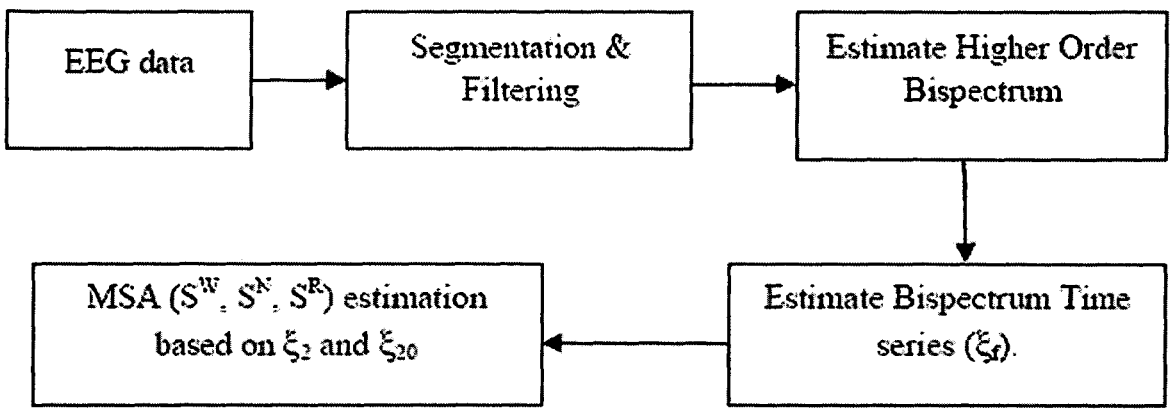
FIG. 2 is a flowchart of a method for estimating macro sleep architecture states of a subject according to an embodiment of the present invention.

The clinical data acquisition environment for this work is the Sleep Diagnostic Laboratory of The Prince Alexandra Hospital, Australia. The data was recorded using clinical Polysomnography (PSG) equipment (Siesta, Compumedics®, Sydney, Australia). Patient preparation, electrode placement and instrumental set-up were done by an experienced sleep technician according to AASM guidelines [9]. Table 3 describes the demographic details of the subjects studied.

Database A: From each subject in this database, routine PSG data was collected. In a typical PSG test, signals such as ECG, EEG, EMG, EOG, nasal/oral airflow, respiratory effort, body positions, body movements and blood oxygen saturation are monitored. EEG data was recorded from both hemispheres using electrode positions C4, C3, A2, and A1, based on the standard international 10-20 system of electrode placement [10] illustrated in FIG. 2A. The subject population includes individuals with symptoms such as daytime sleepiness, snoring, tiredness, lethargy etc and are suspected of sleep apnoea. They were referred to the hospital for a routine PSG test.

Database B: In this database, EEG data from 19 different positions (see FIG. 13) on the skull were recorded in addition to the conventional PSG channels described under Database A above. Electrode locations were as specified in the Standard 10-20 system of EEG electrode placement [10]. The data recorded in this database were from healthy volunteers, defined as individuals without any symptoms of the OSAHS syndrome.

Database C: This database contains data from the subjects referred for the Multiple Sleep Latency Test (MSLT) [28] or Maintenance of Wakefulness Test (MWT) [6]. Typical physiological signals which are recorded in MSLT and MWT are (i) 4 channels of EEG (C3, C4, O1, O2 with reference to A1 and A2). (ii) left and right eye Electrooculograms (EOGs), and (iii) submentalis electromyogram (EMG).

The collected data was segmented into sub-records of length M samples for further analysis. Note: In the field of sleep medicine these segments are conventionally termed as epochs. So from here onward they will be referred to interchangeably as epochs or segments.

HOS-Based Analysis of EEG

Let $x^i(k)$, $i=1, 2, 3 \ldots, N$, denote the k-th sample of the i-th segment of digitized EEG data where N is the total number of segments in a recording. The samples $x^i(k)$ are modelled as:

$$x^i(k) = h^i(k) = e^i(k) + w^i(k) \tag{1}$$

where $e^i(k)$ is a white non-Gaussian process, and $h^i(k)$ is a stable, possibly non-minimum phase kernel representing the underlying system generating the EEG segment $x^i(k)$. The term $w^i(k)$ represents measurement noise within the frequency band of interest, which is traditionally modelled as a white Gaussian process. The inventors have relaxed this constraint and allow the measurement noise to be either a white or colored Gaussian noise, or, any noise process with a symmetrical probability density function.

A method according to an embodiment of the present invention will now be described that discounts noise processes $e^i(k)$ and $w^i(k)$ and capture the features of the underlying EEG generating mechanism via the kernel $h^i(k)$ thereby enabling classification of EEG into REM/NREM/WAKE stages, as well as enable us to define a measure of sleepiness. The inventors achieve that in the $3^{rd}$-order spectra domain in order to keep the phase information in $h^i(k)$ intact. While the third order spectra is preferred by the inventors and an implementation discussed on the third order spectra is described in detail herein other spectra of order greater than two may also be used. For example the fourth order spectrum, i.e. the trispectrum might be employed.

The Bispectrum Estimation

The third order spectrum of a signal is known as the bispectrum. The bispectrum can be estimated as the 2D Fourier transform of the third order cumulant sequence $C^{xi}(\tau1,\tau2)$ [29]. Transforming (1) to the Cumulant domain, we obtain:

$$C^{xi}(\tau1,\tau2) = E\{x^i(k) \cdot x^i(k+\tau1) \cdot x^i(k+\tau2)\} \tag{2}$$

where the sequence $x^i(k)$ is assumed to be zero mean. (If this condition is not satisfied, we can easily subtract the mean of the signal to make it zero mean). The bispectrum $B^{xi}(\omega1,\omega2)$ of $x^i(k)$ is given by, $$B^{xi}(\omega1,\omega2) = \gamma \cdot H(\omega1) \cdot H(\omega2) \cdot H^*(\omega1+\omega2) + B^{wi}(\omega1+\omega2) \tag{3}$$

where $H(\bullet)$ is the one dimensional Fourier transform of $x^i(k)$, $\gamma$ is the skewness of $e^i(k)$, and $B^{wi}(\omega1,\omega2)$ is the bispectrum of the noise process wi. Since the bispectrum of a Gaussian process is zero, $B^{wi}(\omega1,\omega2)=0$, leaving a high SNR signal:

$$B^{xi}(\omega1,\omega2) = \gamma \cdot H(\omega1) \cdot H(\omega2) \cdot H^*(\omega1+\omega2) \tag{4}$$

which depends on the EEG system response $h^i(k)$.

The bispectrum obtained using (4) will be a complex number. Unlike the power spectrum ($2^{nd}$ order statistics) based on the autocorrelation, bispectrum preserves Fourier phase information. Thus, the inventors have conceived that the EEG System Response $h^i(k)$ can be estimated from the bispectrum keeping the true Fourier phase intact. In contrast, power spectrum (or autocorrelation based) techniques lose phase information, and the EEG System Response estimated from it will be the minimum-phase equivalent of the original response.

Equation (4) points out that $B^{xi}(\omega1,\omega2)$ carries information on the EEG system response which, the inventors have realised, provide diagnostic features to score sleep. Note that the response $H(\omega)$ appears in (4) as a non-linearly transformed quantity. $B^{xi}(\omega1,\omega2)$ is a multi-dimensional signal, and using it to derive features for staging sleep can be difficult.

In [30] the problem of signal reconstruction from the bispectrum was considered, and it was proved that any 1-dimensional slice of the bispectrum carries sufficient information to estimate a system response within a time-shift, as long as the chosen slice is not parallel to any one of the frequency axes or to the diagonal at 135 degrees. The inventors have understood that such a result may be utilized, in a preferred embodiment of the invention, to reduce the computational complexity of the HOS techniques and to identify features easily for sleep staging. The flexibility offered by the choosing of arbitrarily oriented and shifted oblique slices is also advantageous in avoiding unfavourable regions in the Bispectrum.

In the frequency domain, a quantity $P_i(\omega;\phi,\rho)$ can be defined for each data segment $x_i(k)$ such that $P_i(\omega;\phi,\rho) = B^{xi}(\omega, \phi\omega+\rho)$ describes a one-dimensional slice inclined to the $\omega_1$-axis at an angle $\tan^{-1}\phi$ and shifted from the origin along the $\omega_2$-axis by the amount $\rho$, $(-\pi<\rho<\pi)$ [30].

2.22 The Slice-Bispectrogram and the Bispectrgram Time Series (BTS)

The slice $P_i(\omega;\phi,\rho)$ carries complete information on the EEG system response (i.e. the underlying EEG generating system) according to the model we have adopted. Thus, in order to describe the overnight data in a graphical way, we define a matrix $S_B(\omega;\phi,\rho)$ such that:

$$S_B(\omega;\phi,\rho) = [P_0(\omega;\phi,\rho)|P_1(\omega;\phi,\rho)| \ldots P_i(\omega;\phi,\rho), \ldots P_{N-1}(\omega;\phi,\rho)] \tag{5}$$

where the $i^{th}$ column of $S_B$ represents a vector $[P_i(\omega;\phi,\rho), -\pi<\omega<\pi]^T$. We call this matrix the Slice-Bispectrogram. When displayed as an image, it illustrates the time evolution of the slice $P_i(\omega;\phi,\rho)$ during the course of the night.

The inventors have conceived that features to stage sleep into REM/NREM/WAKE stages can be derived from $S_B(\omega;\phi,\rho)$. A set of times series, called Bispectrum-Time-Series (BTS, $\xi_f$), is formed by considering a set of fixed $\omega$, i.e. $\omega=\omega_0, \omega=\omega_1, \omega_2 \ldots \omega_{N-1}$ as follows:

$$\text{Time series } 0(\xi_0): S_B(\omega_0; \phi, \rho) = \begin{Bmatrix} P_0(\omega_0; \phi, \rho), P_1(\omega_0; \phi, \rho), \ldots, \\ P_i(\omega_0; \phi, \rho), \ldots, P_{N-1}(\omega_0; \phi, \rho) \end{Bmatrix},$$

$$\text{Time series } 1(\xi_1): S_B(\omega_1; \phi, \rho) = \begin{Bmatrix} P_0(\omega_1; \phi, \rho), P_1(\omega_1; \phi, \rho), \ldots, \\ P_i(\omega_1; \phi, \rho), \ldots, P_{N-1}(\omega_1; \phi, \rho) \end{Bmatrix},$$

$$\vdots$$

$$\text{Time series } N-1(\xi_{N-1}): S_B(\omega_{N-1}; \phi, \rho) =$$

$$\begin{Bmatrix} P_0(\omega_{N-1}; \phi, \rho), P_1(\omega_{N-1}; \phi, \rho), \ldots, \\ P_i(\omega_{N-1}; \phi, \rho), \ldots, P_{N-1}(\omega_1; \phi, \rho) \end{Bmatrix}.$$

Symbol $\xi_f$ represents the Bispectrum-Time-Series at frequency f. The inventors have found that it is possible to choose particular values for 'f' such that the Bispectrum-Time-Series, $\xi_f$ carries sufficient information to characterize macro-sleep-stages. In Section 3, the implementation details to estimate MSA will be explained with derived results.

Results and Discussion

Implementation details of a method according to a preferred embodiment of the invention will now be described. The results of the method will then be compared to a set of clinical data with a view towards exploring the method's performance.

Figure 2A:
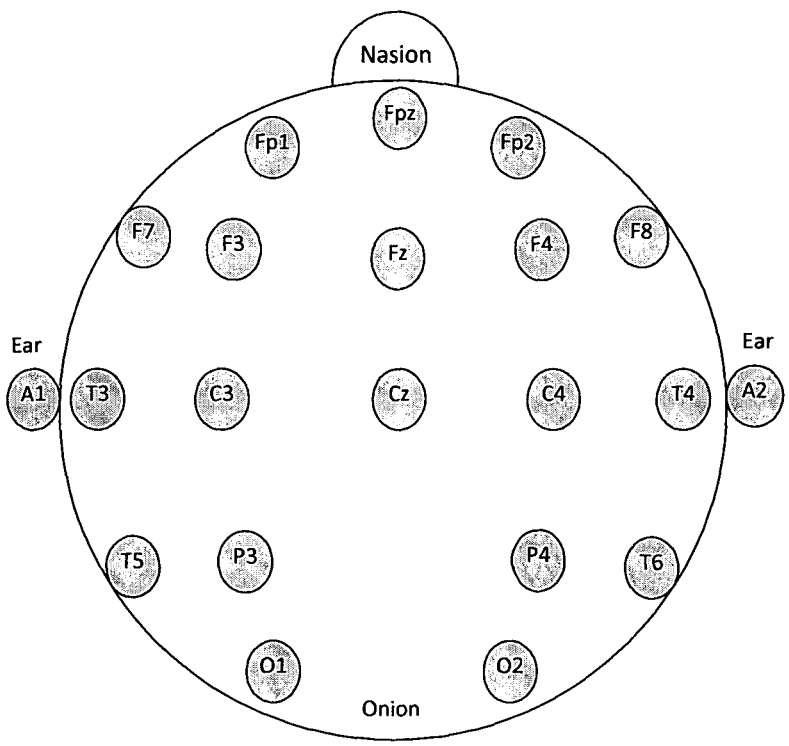
FIG. 2A is a plan view of a human head indicating electrode placement positions.

FIG. 2 shows a block diagram according to an embodiment of the present invention. The following discussion will describe the method which entails processing EEG signals, or EEG signal data, to produce indications as to which MSA states segments of the EEG signals correspond to and in one embodiment a sleepiness index. The various steps of the method are programmed as tangible instructions in a computer readable media for execution by one or more processors of the computer. The computer may include a suitable analog to digital converter to receive EEG signals from electrodes that are in contact with a patient. Alternatively, the computer may process previously logged EEG signals stored on a magnetic, electronic memory or optical medium for example.

Implementation Details

A). Pre-filtering of EEG Segments:

EEG is a low-frequency signal and the frequency band of present interest is contained within 1-45 Hz. Thus $x^i(k)$ is filtered using a $5^{th}$ order, zero-phase digital Butterworth bandpass filter f(k) with lower cut-off frequency $f_l=1$ Hz and higher cut-off frequency $f_h=45$ Hz to remove out-of-band noise, including the ubiquitous power line interference at 50 Hz. All results shown herein have been derived with filtered EEG data. Let the filtered segments $x^i(k)$ be denoted by $y^i(k)$.

B). Estimation of the HOS:

The bispectrum can be estimated via estimating the $3^{rd}$ order cumulant (see (2)) and then taking a 2D-Fourier transform (see (3)), this method, known as the indirect method of estimating the bispectrum, is used in the preferred embodiment of the invention discussed herein. The procedure to form the estimate $C^{yi}(\tau 1, \tau 2)$ of the cumulant $C^{yi}(\tau 1, \tau 2)$ of $y^i(k)$ is outlined in steps (S1)-(S4) below.

(S1) Segment $y^i(k)$ into J records of length L samples each. Subtract the mean of each record to form the zero-mean sub-segments $y^{ij}(k)$. Estimate the $3^{rd}$ order cumulants $\overline{C}^{yij}(\tau_1, \tau_2)$ of each sub-segment $y^{ij}(k)$ using (6) as defined in [30].

$$c^{yij}(\tau_1, \tau_2) = \frac{1}{L}\sum_{k=0}^{L-1} y^{ij}(k)y^{ij}(k+\tau_1)y^{ij}(k+\tau_2),$$
$$|\tau_1| \le Q, |\tau_2| \le Q$$

(6)

where Q is the length of third-order correlation lags considered in the computation.

(S2) Average the cumulants estimates $\overline{C}^{yij}(\tau_1, \tau_2)$ over all sub segments $j=0, 1, \ldots J-1$ to obtain the overall cumulant estimate $\overline{C}^{yi}(\tau_1, \tau_2)$.

$$C^{yi}(\tau_1, \tau_2) = \frac{1}{J}\sum_{j=0}^{j-1} \overline{C}^{yij}(\tau_1, \tau_2)$$

(7)

(S3) Apply a bispectrum window function to the overall cumulant estimate $\overline{C}^{yi}(\tau_1, \tau_2)$ to obtain the windowed cumulant function $C_w^{yi}(\tau_1, \tau_2)$. We used the minimum bispectrum-bias supremum window described in [29] for the purpose.

(S4) The bispectrum $B^{yi}(\omega_1, \omega_2)$ of the segment $y^i(k)$ was estimated as the 2-D Fourier transform of the cumulant estimate $\overline{C}_w^{yi}(\tau_1, \tau_2)$.

$$B^{yi}(\omega_1,\omega_2)=\Sigma_{T_1=-c}^{T_1=+c}\Sigma_{T_2=-c}^{T_2=+c}C^{yi}(\tau_1,\tau_2)e^{-j(\tau_1e_1+\tau_2e_2)}$$

(8)

It should be noted however that the bispectrum slice may also be estimated directly in the frequency domain as $$B^{yi}(\omega_1,\omega_2)=\gamma \cdot Y^i(\omega_1) \cdot Y^i(\omega_2) \cdot Y^{i*}(\omega_1+\omega_2)$$

(8A)

where $Y^i(\omega_1)$ is the 1-Dimensional Fourier transform (1D FFT) of the measured, filtered EEG signal and y is the skewness of $y^i$.

FIG. 3 shows typical mesh and contour plots of the bispectrum magnitude $Abs(B^{yi}(\omega_1,\omega_2))$ during different macro sleep states, $S^W$, $S^N$ and $S^R$. Abs (•) stands for the computation of the modulii of each and every entry. The bispectra shown in FIG. 3 were computed from short EEG segment of length 10 s, randomly taken from the EEG data of subject ID 5 (Table 3). The salient features seen in FIG. 3 were consistently observed across the subjects in Databases A, B and C.

According to mesh plots in the FIG. 3, the bispectrum magnitude varies during different sleep states. It is low during the $S^W$ and $S^R$ states and increases considerably during the $S^N$ states. A hypothesis test (two tailed; student-t statistic) showed that the mean bispectrum magnitude during $S^N$ sleep state was different from mean bispectrum magnitude during $S^W$ or $S^R$ states at the level of significance $\sigma=0.001$.

The contour plots of the bispectrum magnitude in the FIG. 3 shows the location of the peaks at different sleep states. The comparison of contour plot for $S^W$ or $S^R$ with that for $S^N$ state, shows that, bispectrum during $S^W$ state have multiple peaks at different frequencies ($\omega \approx 1$-20 Hz) whereas peak in bispectrum magnitude during NREM state is just concentrated in narrow frequency band ($\omega<5$ Hz). Bispectrum during $S^R$ shows multiple peaks in low frequency region ($\omega<10$ Hz), similar to $S^W$ state however, the bispectrum peak at high frequency ($\omega>15$ Hz) completely diminishes during REM states. These features in the EEG bispectrum were consistently seen over the whole night sleep EEG data.

C). Estimation of the Slice-Bispectogram:

Further implementation details of the method described in Section 2.22 will now be discussed. Without a loss of generality (see [30]), set $\phi=1$ and set $\rho=0$ so that the slice of the bispectrum considered is inclined to the $\omega_1$-axis by 45 degrees and passes through the origin (i.e. the line described by $\omega_1=\omega_2$ in the ($\omega_1,\omega_2$)-plane) as symbolized by $S_B(2\pi f; 1,0)$.

Figure 4:
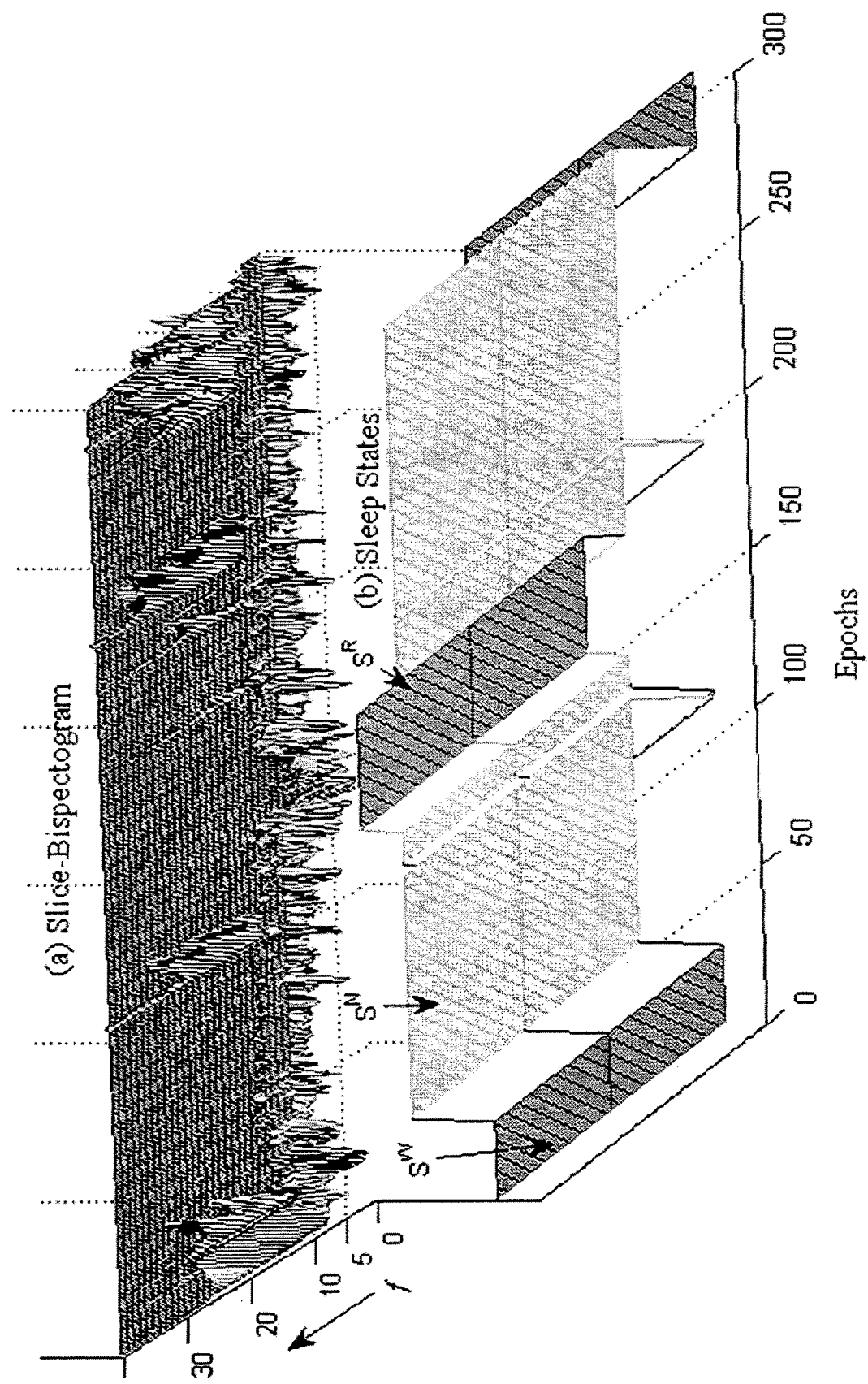
FIG. 4 is a graph illustrating a correspondence between slice-bispectogram and sleep states of a subject.

FIG. 4(a) shows the slice bispectogram magnitude (Abs $(S_B(2\pi f;1,0))$. FIG. 4(b) shows corresponding sleep states scored manually by a sleep technician. Y-axis of FIG. 4(a) is the frequency axis, $f=1$-40 Hz. X-axis of FIG. 4 is the epoch number. In FIG. 4 we display the first contiguous 300 epochs out of the total recorded sleep epochs (N=810) for that particular subject, for the sake of display clarity.

FIG. 4(a) clearly illustrates the variation in the bispectogram magnitude in the different frequency bands with the change in sleep states, consistently over the night. During the $S^W$ states bispectogram shows comparably high magnitude in the higher frequencies. With the appearance of $S^N$ states magnitude in the higher frequencies (f>10) decreased whereas that of the lower frequencies (f<10 Hz) increased. Again as the sleep state changed to $S^R$ states the magnitude in all the frequencies decreased.

D). Estimation of the Bispectrum-Time-Series:

From the Slice-Bispectogram ($S_B$) the, Bispectrum-Time-Series (BTS, $\xi_f$) was estimated at two frequencies $S_B(2\pi f_0; 1,0)$ and $S_B(2\pi f_1;1,0)$. For the results reported herein, the inventors set $f_0=2$ Hz and $f_1=20$ Hz for their ability to discriminate REM/NREM/WAKE states. Note that the entries of BTS are complex valued. The following definitions are used from hereon: $\xi_2 = Abs(S_B(2\pi f_0;1,0))$, and $\xi_{20} = Abs(S_B(2\pi f_1;1,0))$. Once again Abs(•) stands for the computation of the modulii of each and every entry in BTS. The inventors have found that in a preferred embodiment, $\xi_2$ and $\xi_{20}$ can be used efficiently and accurately to identify different macro-sleep states (in MSA) and also to define a sleepiness index via the time-density of micro-sleep events. To make the time-series a dimensionless quantity, normalisation is applied using (8B) before using them for classification.

$$\xi_2(i) = \frac{\xi_2(i)}{sum(\xi_2)} \times 100, \xi_{20}(i) = \frac{\xi_{20}(i)}{sum(\xi_{20})} \times 100 \quad (8B)$$

Figure 5:
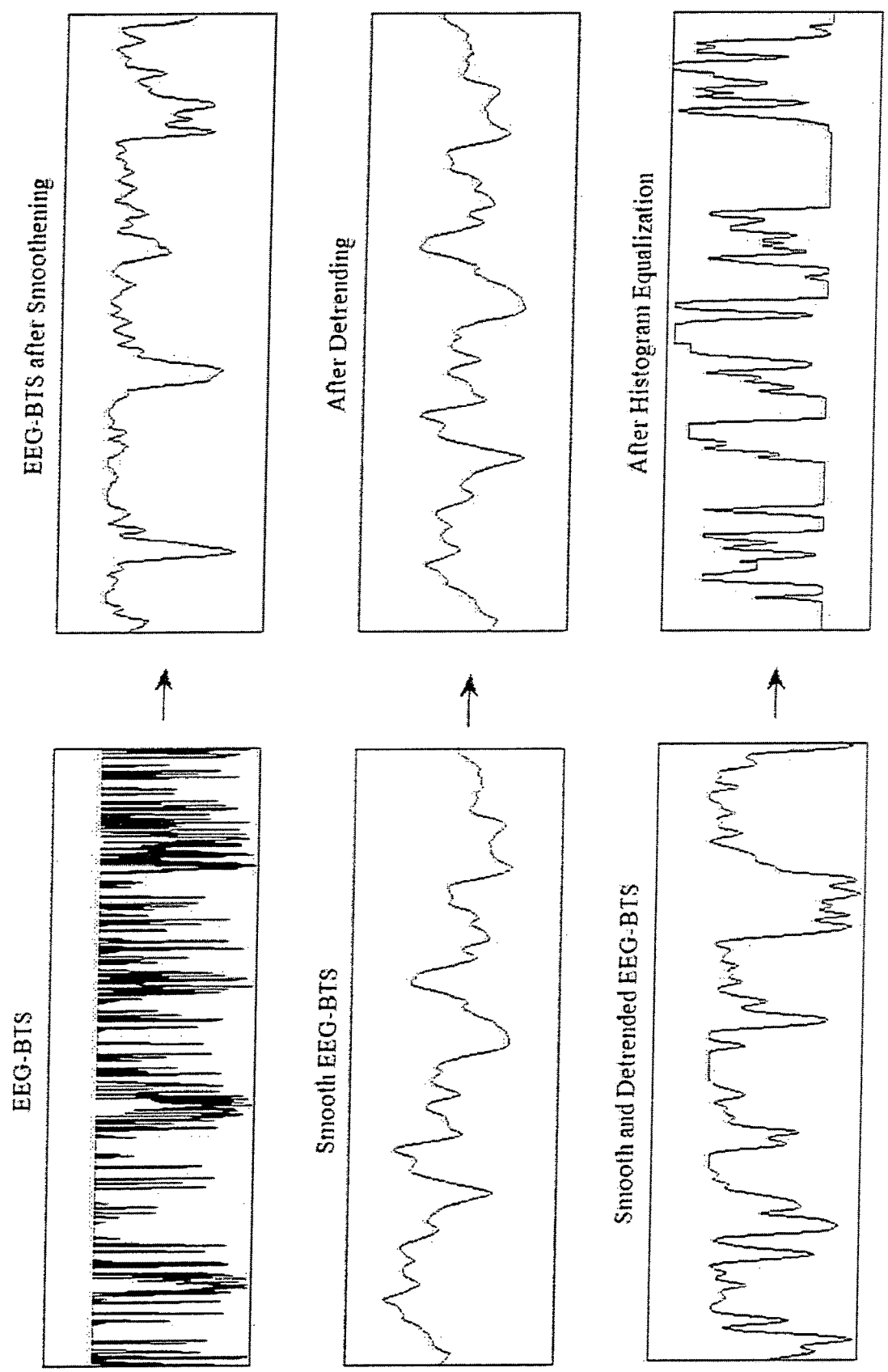
FIG. 5 shows the effect of pre-processing (smoothing, de-trending and equalization) applied to EEG Bispectrum Time Series (BTS).

In the case of $\xi_2$, pre-processing (smoothing, de-trending and equalization) is applied before using the time series in classification work in order to improve the performance; $\xi_{20}$, however did not require such processing. To reveal the slow changes and remove the outliers from $\xi_2$, 'Loess Smoothening Method [31, 32] is used, which is based on local regression using weighted linear least squares and a $2^{nd}$ degree polynomial model. De-trending with a least-squares-fit straight line was used to remove the trend in $\xi_2$. Histogram equalization is often used in image processing to increase the contrast of the image. In the presently described embodiment, histogram equalization is applied to $\xi_2$ after the steps of smoothening and de-trending to obtain the time series $\xi'_2$. FIG. 5 shows the effect the pre-processing on $\xi_2$.

Figure 6:
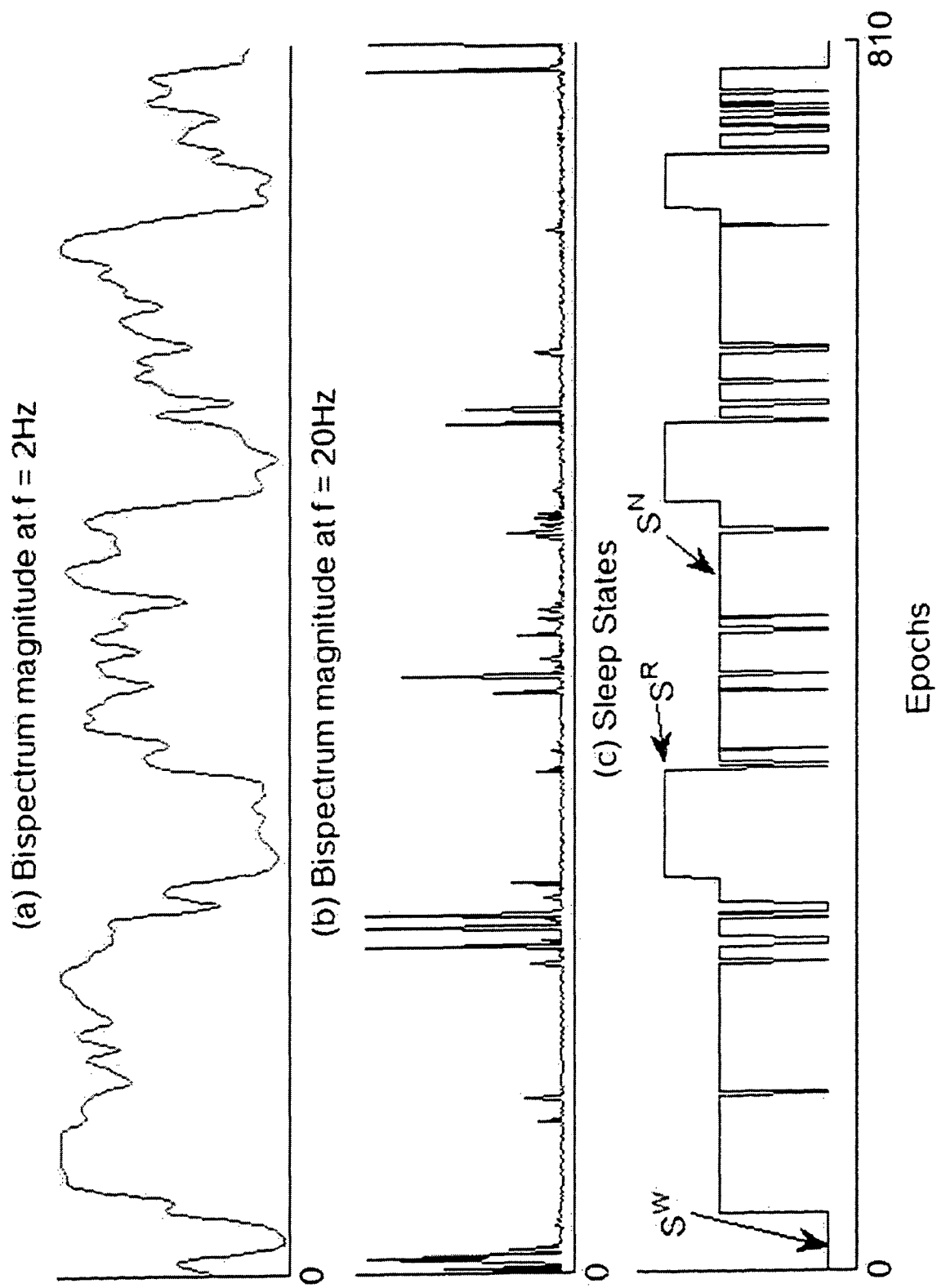
FIG. 6 compares graphs of bispectrum magnitudes at 2 Hz and 20 Hz with technician scored macro sleep states.

FIG. 6(a) and FIG. 6(b) show the $\xi_f$ at frequencies 2 Hz and 20 Hz respectively. FIG. 6(c) shows technician scored macro sleep states. EEG data $x^i(k)$ for this figure is taken from subject ID 6 of Database A, Table 3. FIGS. 6(a), 6(b) and 6(c) illustrate explicitly the characteristics of Slice-Bispectogram. The magnitude of 2 Hz component varies in a cyclical fashion, synchronously with the macro sleep states. Magnitude is high during the $S^N$ sleep states and it decreased during $S^R$ and $S^W$ states. The magnitude of the 20 Hz component consistently remained low during the sleep; however it increased considerably with the episodes of $S^W$ states during the night. Thus, $\xi_{20}$ is a preferred platform for separating wake from other sleep states.

Figure 7:
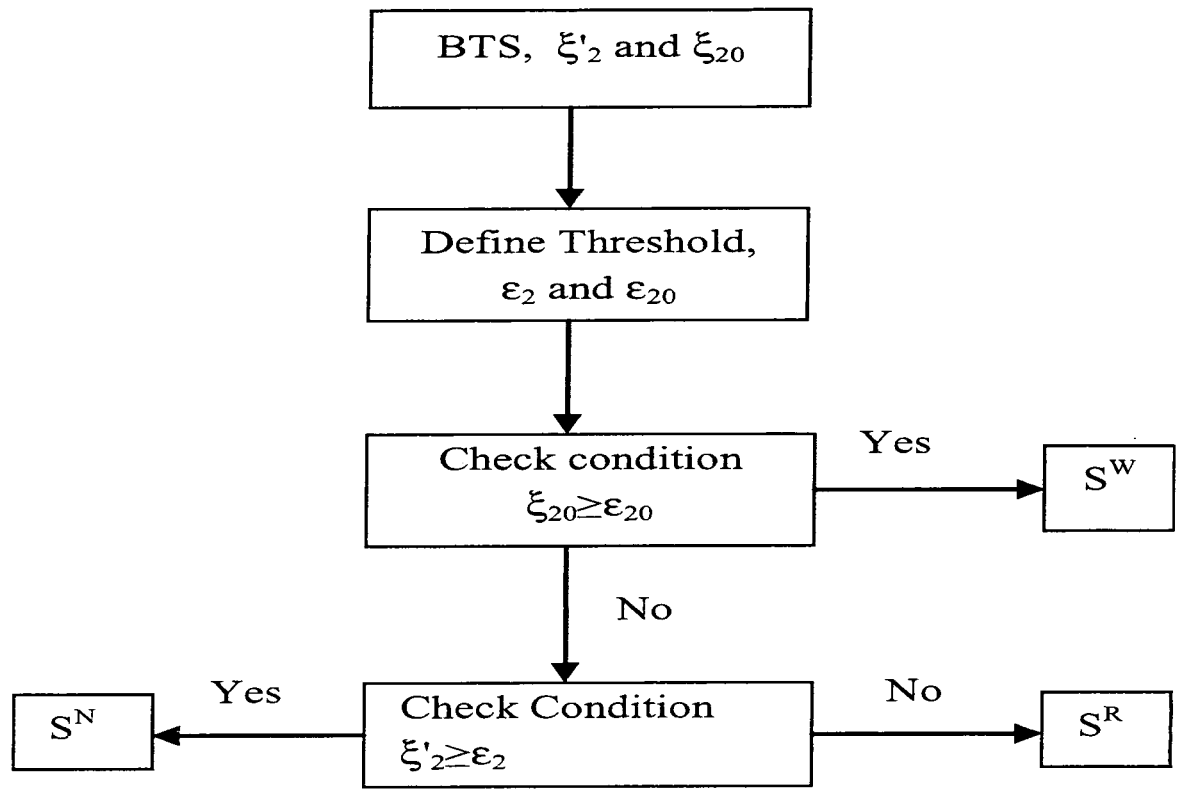
FIG. 7 is a flowchart of a method for determining MSA from two bispectrum time series according to a preferred embodiment of the present invention.

The steps for estimating the MSA from the two bispectrum time series $\xi_{20}$ and $\xi'_2$ according to the preferred embodiment, will now be described. The following method is also illustrated in the flowchart of FIG. 7.

E). MSA Scoring Algorithm Based on Bispectrum Time Series $\xi'_2$ and $\xi_{20}$ Bispectrum time series, $\xi_{20}$ and $\xi'_2$ were used to classify each data segment $x^i(k)$ (see (1)) into the classes WAKE ($S^W$)/REM ($S^R$)/NREM ($S^N$) sleep. The length of data segments (M) were set to the standard 'epoch length' of M=30 s as used in routine sleep scoring.

The classification of the segment $x^i(k)$ into the two categories WAKE/SLEEP can be done quite easily based on $\xi_{20}$ (see FIG. 6(b)). However, it cannot be used to differentiate between SLEEP states NREM and REM. The series $\xi'_2$ can be used easily to identify NREM segments, but cannot be used to separate WAKE from REM stages. According to the preferred embodiment of the invention, both $\xi_{20}$ and $\xi'_2$ are used together in a sequential decision process to classify $x^i(k)$ into the three categories $S^W/S^R/S^N$ sleep.

The identification of sleep states was done based on direct threshold operations on the $\xi'_2$ and $\xi_{20}$ as described in steps (T1)-(T3) below:

(T1) WAKE/SLEEP Classification: For classifying each i=1, 2, 3 ... N, segments of EEG data $x^i(k)$ into $S^W$ and SLEEP ($S^R/S^N$) states we used $\xi_{20}$. We set a threshold $\varepsilon_{20}$ computed from $\xi_{20}$. The condition $\xi_{20} \geq \varepsilon_{20}$ was tested for all the N segments. If condition $\xi_{20} \geq \varepsilon_{20}$ is true in a segment then that segment was classified as $S^W$ else as SLEEP.

(T2) NREM/REM Classification: After the step (T1), the EEG data segments are separated into two states WAKE and SLEEP. To further classify sleep segments into NREM and REM sleep, used $\xi'_2$ is used. The threshold $\varepsilon_2$ is previously computed from $\xi_2$. The condition $\xi_2 \geq \varepsilon_2$ is tested in each segment previously classified as Sleep in step (T1). If the condition is satisfied then that segment is classified into NREM sleep else into REM sleep. The method for calculating proper thresholds ($\varepsilon_2$ and $\varepsilon_{20}$) is described in Appendix F.

(T3) Estimation of Sleep Parameters: From the estimated sleep states of each patient, we computed TST, SE, RSL and percentage of $S^W$, $S^R$ and $S^N$ sleep, using the standard definition given in Appendix B.

3.2 Performance Evaluation of the MSA Scoring Method on Clinical Data

For the purposes of this specification, macro sleep states estimated using the preferred embodiment of the present invention are termed the HOS based Estimated Sleep States (HESS), and the reference states estimated by the expert human scorer is called the Technician Scored Sleep States (TSSS). The TSSS will be considered the ground truth, against which the performance of the HESS will be compared.

The performance of the HESS was evaluated on a clinical database of EEG/PSG data (see Table 3.1, Database-A), and compared with that of the TSSS estimate. In order to test the stability and reliability of the algorithm, subjects with varying degrees of OSAHS severity were included. The test subjects population (23 subjects) had the mean RDI of 27.23±26.24, ranging from as low as 0.6 and as high as 94.4. The mean arousal index (ArI) for the subject population was 29.05±19.23.

To compute the HESS, EEG data from only one channel is required. In Database A, EEG data were recorded with the electrode positions C4, C3, A1 and A2 based on the standard international 10-20 system of electrode placement. The results presented in this section are based on the EEG data from the electrode position 'C4' with reference to 'A2'.

To compute the TSSS, an expert human Sleep Scientist manually scored PSG data based on R&K criteria [7] and clinical practice parameters formulated by the AASM. As known from previous studies, the intra-scorer variability for the Sleep Scientist was 84%. According to the TSSS scoring, of the total of 20,714 epochs from the 23 subjects, 3508 were in $S^W$, 14098 were in $S^N$ and 3108 were in $S^R$.

The performance of the HESS in scoring macro sleep states was evaluated in several different ways. Using TSSS as the ground truth, the following performance measures were computed:

Sensitivity, Accuracy and the Positive Predictive Value (PPV).

The agreement between TSSS and HESS using Cohen's Kappa statistic [31] (please see Appendix D on how to interpret Kappa values).

Pearson's correlation coefficient and Altman-Bland plots [34] were used for the descriptive analysis of TST, SE, RSL and percentage of $S^W$, $S^N$, $S^R$ sleep computed from HESS.

Hypothesis testing to establish the statistical significance of the results at the level of significance $\sigma$=0.001.

Figure 9:
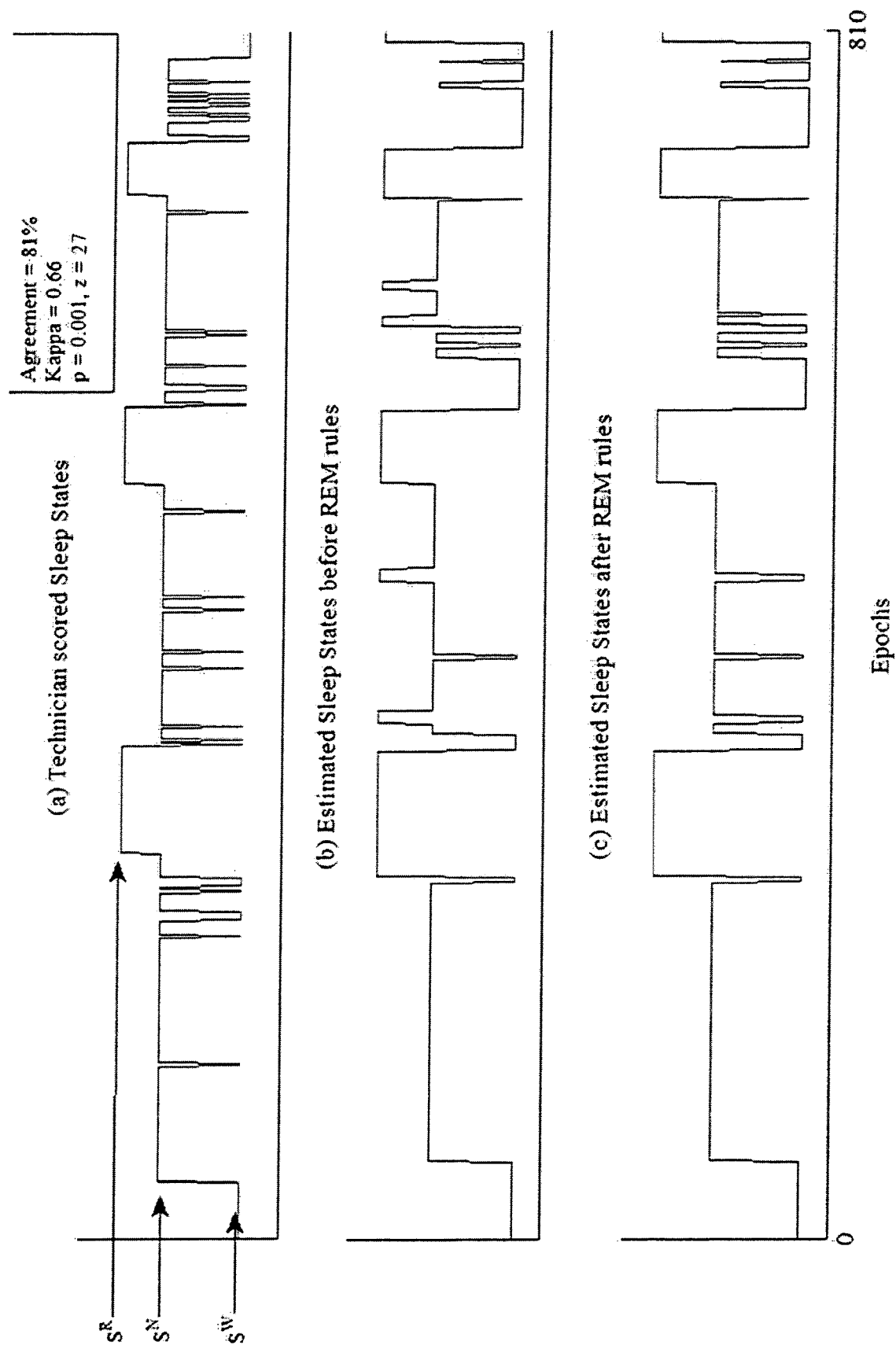
FIG. 9 illustrates PSG scored sleep states compared with automated estimated sleep states determined by a method according to an embodiment of the invention.
Figure 10:
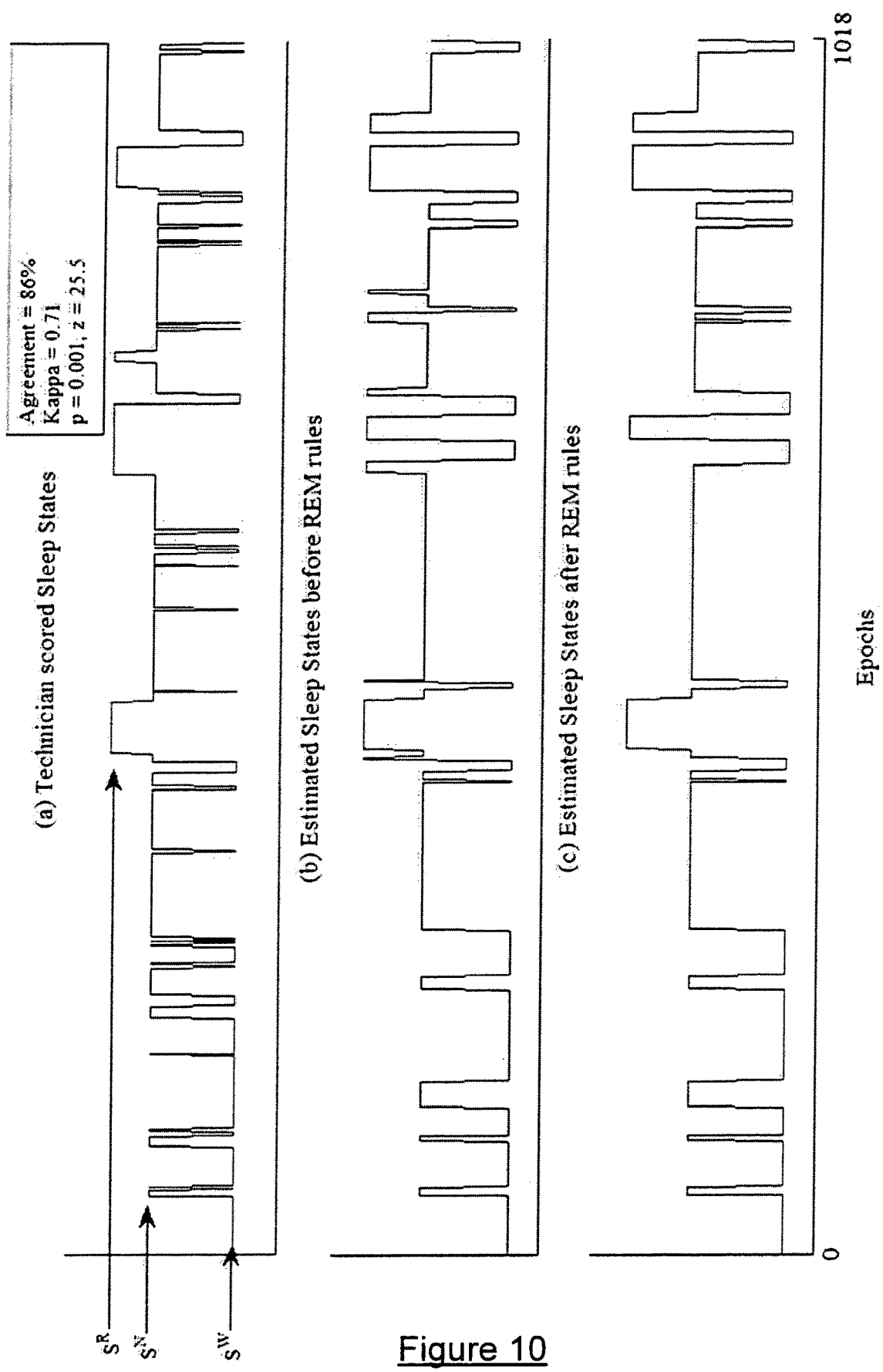
FIG. 10 illustrates PSG scored sleep states compared with automated estimated sleep states determined by a further embodiment of the invention.

FIG. 9 (a)-(b) and FIG. 10 (a)-(b) shows the PSG scored sleep states and automated estimated sleep states after Step (T2) of section 3.1 (E), for two subjects (Subject ID=6 and 19). According to these figures there is high resemblance between the technician scored sleep states and automated sleep states. The agreement between TSSS and HESS in classifying N epochs (N=810 for subject 6 and N=1018 for subject 19) into $S^W$, $S^N$ and $S^R$ was 78% (kappa 0.61) and 80% (kappa=0.69) respectively for FIG. 9 (b) and FIG. 10 (b).

In FIG. 9(b) and FIG. 10(b) a few brief episodes of REM are seen, which are not REM sleep episodes according to TSSS. From the literature it is known that the duration of a typical REM episode is between 10-20 minutes in first sleep cycle which increases in the latter half of the night. Hence, in order to decrease False positive prediction of the REM episodes and to increase the accuracy of HESS a REM-continuity rule was used. According to this rule those periods of REM sleep were targeted which were for less than D mins. These periods of $S^R$ sleep were reclassified into either $S^N$ state or $S^W$ states. For the reclassification a new threshold $\varepsilon'_{20}$ was defined from the $\xi_{20}$ time series. Appendix F shows the method to compute D and $\varepsilon'_{20}$. In the preferred embodiment of the present invention D=8 min and $\varepsilon'_{20}$=min ($\xi_{20}$). If condition $\xi_{20}=\varepsilon'_{20}$ was satisfied then that epoch was classified as $S^W$ else as $S^N$.

FIG. 9(c) and FIG. 10(c) shows the HESS results after applying REM combining rule. After the rule agreement between TSSS and HESS increased to 81% (kappa=0.66, σ=0.001) and 86% (kappa=0.71, σ=0.001) respectively for FIG. 9 and FIG. 10. REM combining rule was used in all the further classification.

Table 5 shows the contingency table, comparing the scoring performance of the HESS with that of TSSS. Table 6 gives the sensitivity, accuracy and PPV statistics for HESS computed from the Table 5. The overall agreement between TSSS and HESS in separating the 20,714 epochs into the two states Sleep ($S^N$ and $S^R$ pooled together) and Wake is 83.78% (kappa=0.48, σ=0.001, z=61). Also, there was a high agreement between TSSS and HESS in classifying $S^W$, $S^N$ and $S^R$ states, of 75.17% (kappa=0.54, σ=0.001, z=94). Table 7 lists the agreement and kappa values between TSSS and HESS for all the 23 subjects. The mean agreement between TSSS and HESS for 23 subjects was 77.6%±7.2% and mean kappa value was 0.58±0.08.

In the PSG test several sleep parameters such as, Total sleep time (TST), Sleep efficiency (SE), REM sleep latency (RSL) and percentage of $S^W$, $S^N$, $S^R$ sleep are directly computed from the scored MSA. Accurate estimation of these parameters substantially depends on the precise classification of macro sleep states. These parameters were computed for each patient from the HESS and compared with those computed using TSSS.

Figure 11:
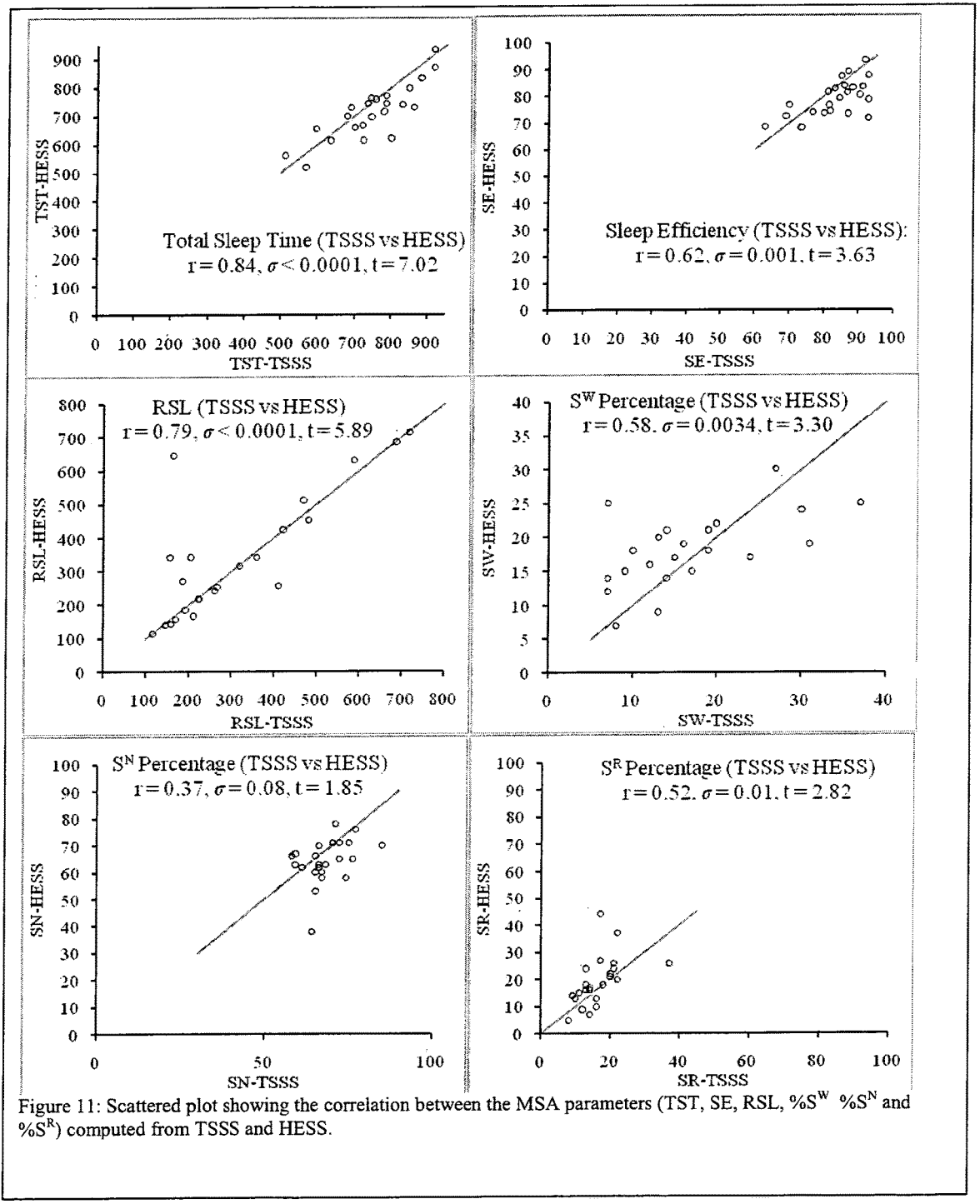
FIG. 11 comprises a number of scatter plots showing the relationship between the parameters Total Sleep Time (TST), Sleep Efficiency (SE), REM Sleep Latency (RSL) and percentage sleep computed using TSSS and HESS.

FIG. 11 consists of scatter plots, showing the relationship between the parameters TST, SE, RSL and percentage sleep computed using TSSS and HESS. The correlation for TST, SE and RSL was 0.84(σ=0.001), 0.62(σ=0.001) and 0.79 (σ=0.001) respectively.

Figure 12:
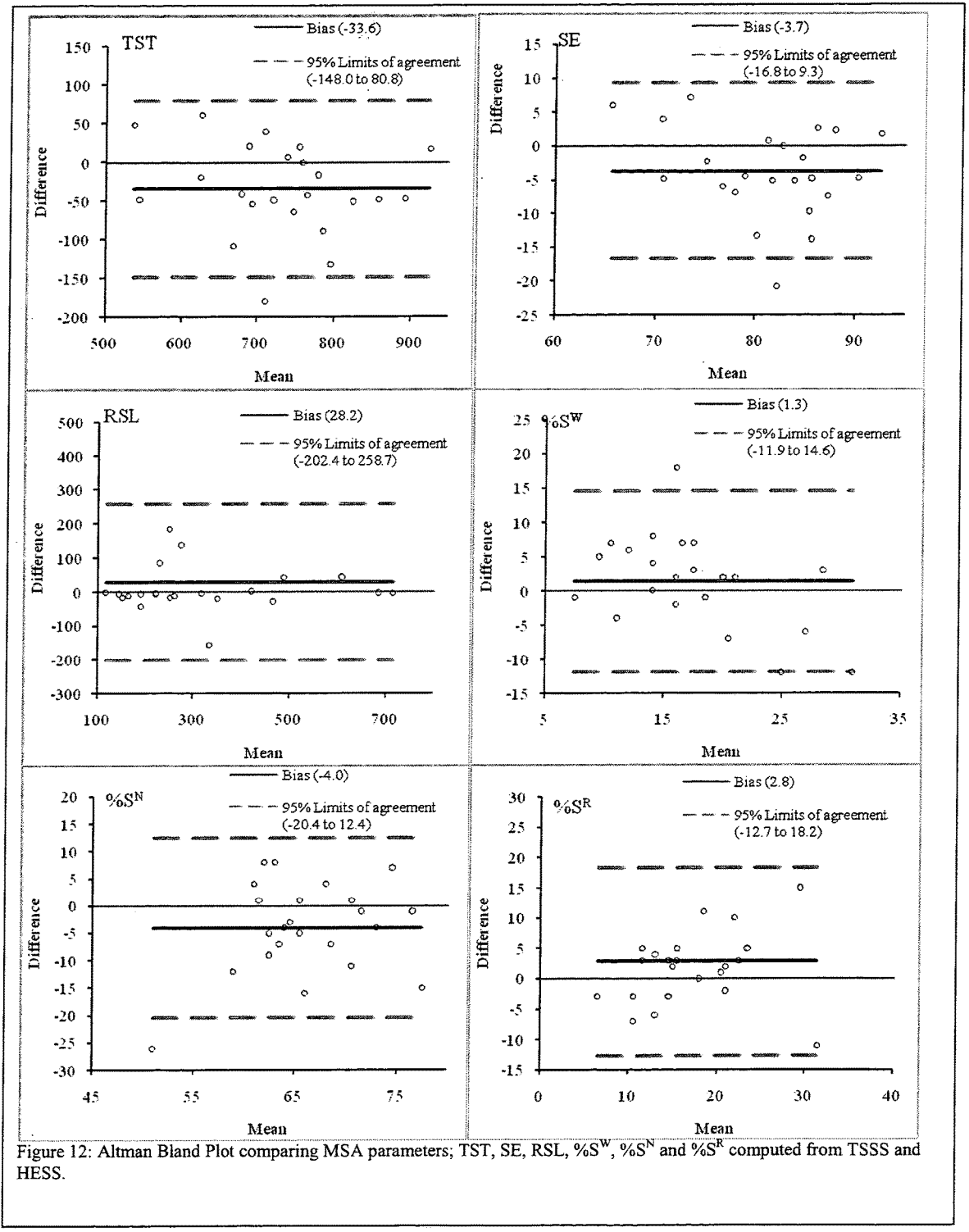
FIG. 12 shows Altman-Bland plots for TST, SE, RSL and percentage sleep and illustrates good agreement between TSSS and HESS in estimating MSA parameters.

FIG. 12 show the Altman-Bland plot for TST, SE, RSL and percentage sleep. These plots show that there is a good agreement between TSSS and HESS in estimating MSA parameters with very small insignificant bias. The bias for TST was −16 minutes (σ=0.32) and for SE was only −3.7% (σ=0.24). The bias for RSL and percentage of $S^W$, $S^N$, $S^R$ sleep were also low and insignificant, 14 min (σ=0.26), 1.3% (σ=0.34), −4% (σ=0.13) and 2.8% (σ=0.10) respectively.

3.3 Performance of HESS Algorithm with Other Electrode Position

The performance of the previously described HESS method according to a preferred embodiment of the invention will now be discussed, when EEG from electrode locations other than the traditional (R&K-recommended, 1968) C3, C4, A1 and A2 positions are used. For this data from the subjects in database B, table 3.2 was used. The International 10/20 electrode locations (see FIG. 13), were investigated with a view towards identifying the best electrode locations suitable for single-channel EEG-based sleep scoring.

Following the customary practice in sleep EEG, site Fpz was used for the ground electrode. The reference electrode for measurement sites located on the left hemisphere of the scalp was A1; similarly, measurements on the right hemisphere used A2. This choice of the ground and reference electrodes comply with the R&K recommended measurements on C3 and C4. This makes a direct comparison between the performances of traditional and the HESS-based techniques possible.

Figure 14:
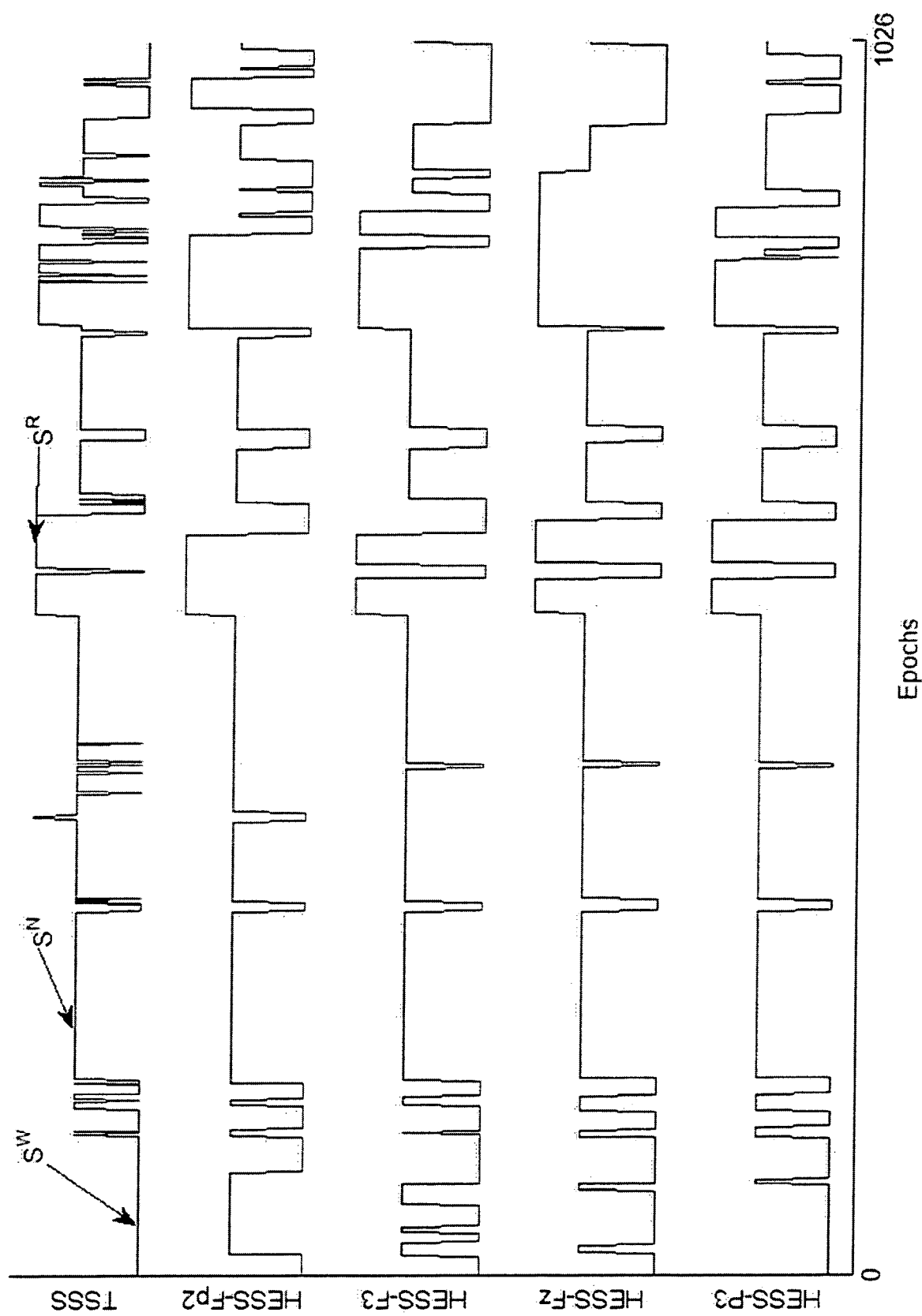
FIG. 14 shows the estimated sleep states using a method according to preferred embodiment of the present invention (herein referred to as HESS) using EEG data from the electrode locations Fp2, F3, Fz and P3 over the scalp.

FIG. 14 shows the estimated sleep states using HESS algorithm using EEG data from the electrode locations Fp2, F3, Fz and P3 over the scalp. Table 8 summarizes the statistical results for all electrodes that were used. A statistically significant (σ=0.0001) agreement between TSSS and HESS for all the electrode positions was found.

3.4 Sleepiness Index

Figure 15:
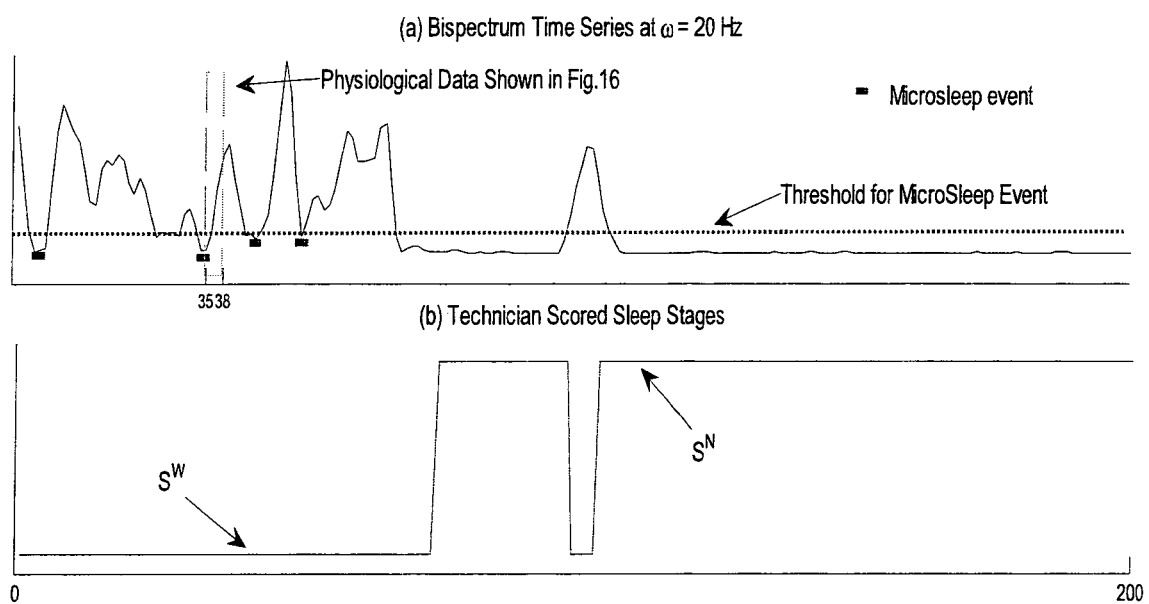
FIG. 15 compares a subject's bispectrum time series to the subjects technician scored sleep stages and indicates microsleep events.

The time series $\xi_{20}$ proved highly successful in classifying EEG epochs into the two groups Sleep and Wake. Wake states correspond to high values of $\xi_{20}$; sleep states are associated with a consistently low magnitude ($s_0$) approaching zero for all practical purposes. It was noted that the magnitude of $\xi_{20}$ gradually moves from a high value towards $s_0$ as a person is falling asleep. Before finally settling down to $s_0$ corresponding to the state Sleep, the magnitude of $\xi_{20}$ briefly touches $s_0$ several times (see FIG. 15 (a)). Such events are associated with EEGs that are characteristic of Sleep, and the inventors define them as micro-sleep events.

According to a preferred embodiment of the present invention, the stability of the $\xi_{20}$ time series to identify micro-sleep events and then use them to form a measure of sleepiness, termed the Sleepiness Index (SI). We define the SI as the fraction of the time the magnitude of $\xi_{20}$ maintained its value corresponding to sleep, i.e., $s_0$, computed over a time frame of 10 seconds. Thus, SI can vary from 0 (no episodes of micro-sleep during the current 10 s period) to 1 (micro-sleep/sleep events completely covers the current 10 s period).

This definition allows the SI index to be computed real time, making it a useful tool to monitor the sleepiness of an individual. Sleep Onset can be defined as the instant at which SI reaches 1, and the Sleep Latency can be defined as the time duration from the 'lights out' to the Sleep Onset. The SI can be applied to automate the scoring of MSLT and the MWT tests, which are two important diagnostic tools used in general sleep medicine. In addition to the use in sleep medicine, the SI-index has the potential to be used in situations such as the sleepiness monitoring of long-range truck drivers; to facilitate this use, SI has been defined in such a way that it can be computed in real-time.

In FIG. 15(a) we show the time series $\xi_{20}$ where a person is falling sleep. The red bars under the series $\xi_{20}$ curve indicate micro-sleep events. The TSSS sleep states are shown in FIG. 15(b). Note that the sleep technologist has not attempted to identify states of micro-sleep. FIG. 15(a) and FIG. 15(b) graphically illustrate the close correspondence of the $\xi_{20}$ and the sleep/wake states of an individual. Moreover, it is seen that the gradual development of sleep over time is captured well by the gradual change in $\xi_{20}$.

Figure 17:
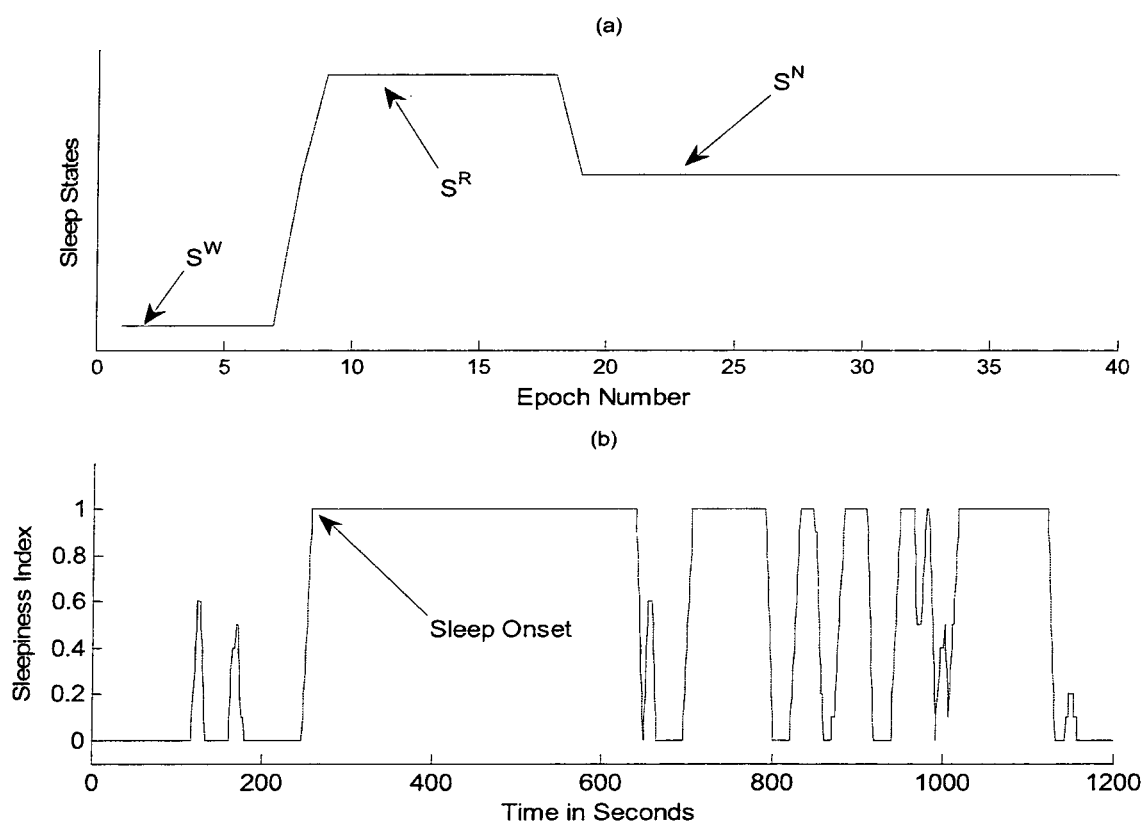
FIG. 17 comprises two graphs comparing sleepiness index (SI), upper graph, determined according to an embodiment of the present invention with technician scored sleep states, lower graph, for a first nap.
Figure 18:
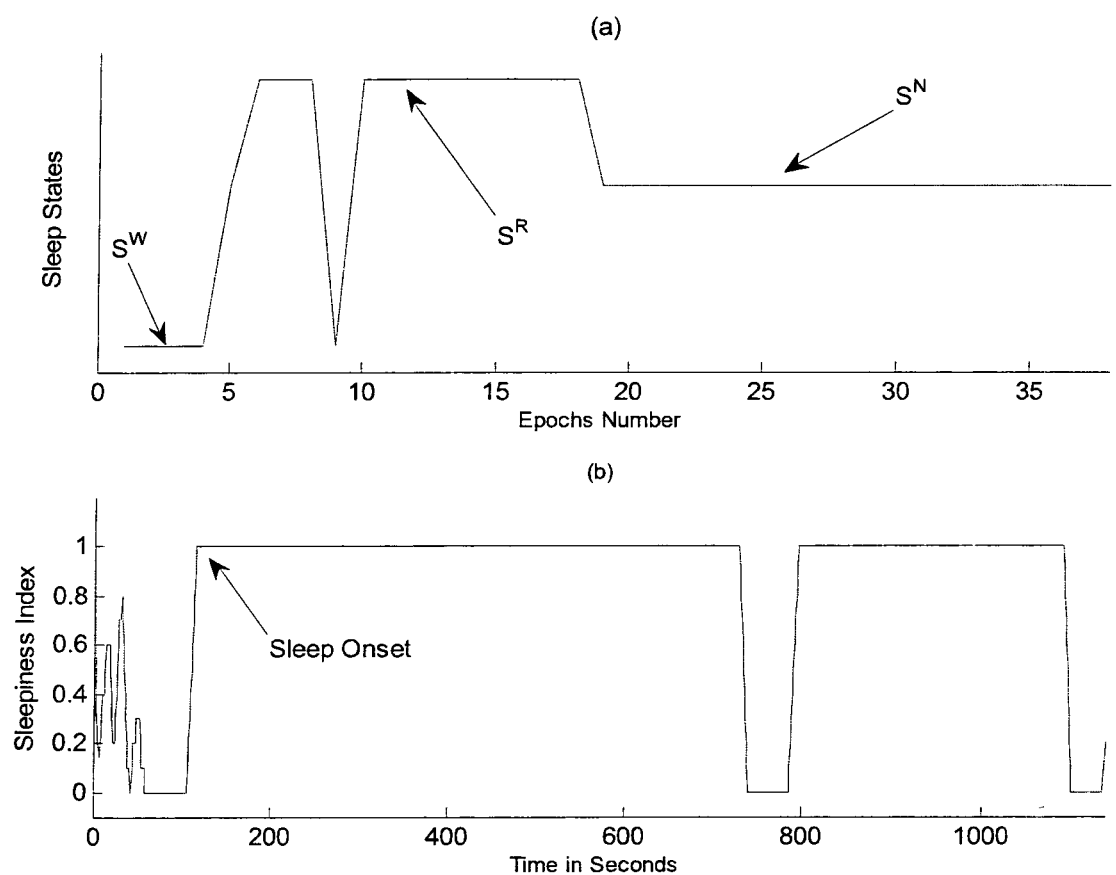
FIG. 18 comprises two graphs comparing sleepiness index (SI), upper graph, determined according to an embodiment of the present invention with technician scored sleep states, lower graph, for a second nap.

To test the capability of the SI to estimate the sleep onset and the sleep latency (SL), we computed SI for the subjects in Database C. In all the computations, the segment length was M=30 s, and the segment overlap was set to 29 s. Thus, the sleep state was assessed every second, based on the data of duration 30 s. The SI index was computed using the sleep state information covering a period of 10 s. FIGS. 17 and 18 shows the SI and TSSS for the subject ID 28. Data in FIG. 17 and FIG. 18 is from the $2^{nd}$ and $3^{rd}$ nap of the MSLT test (see Appendix E for details of the MSLT test). Table 9 gives the SL as computed from the SI and TSSS for all the 4 naps in the MSLT for all the subjects in database C.

According to Table 9, the SL computed via the SI closely matches the Sleep Technologist identified Sleep Latency. The SI based approach, however, has been fully automated and provides consistent results. It does not depend on multiple physiological signals; only one channel of EEG is sufficient for the purpose. On the contrary, Sleep Technologist requires multiple signals and depends on subjective methods to estimate the SL.

Figure 16:
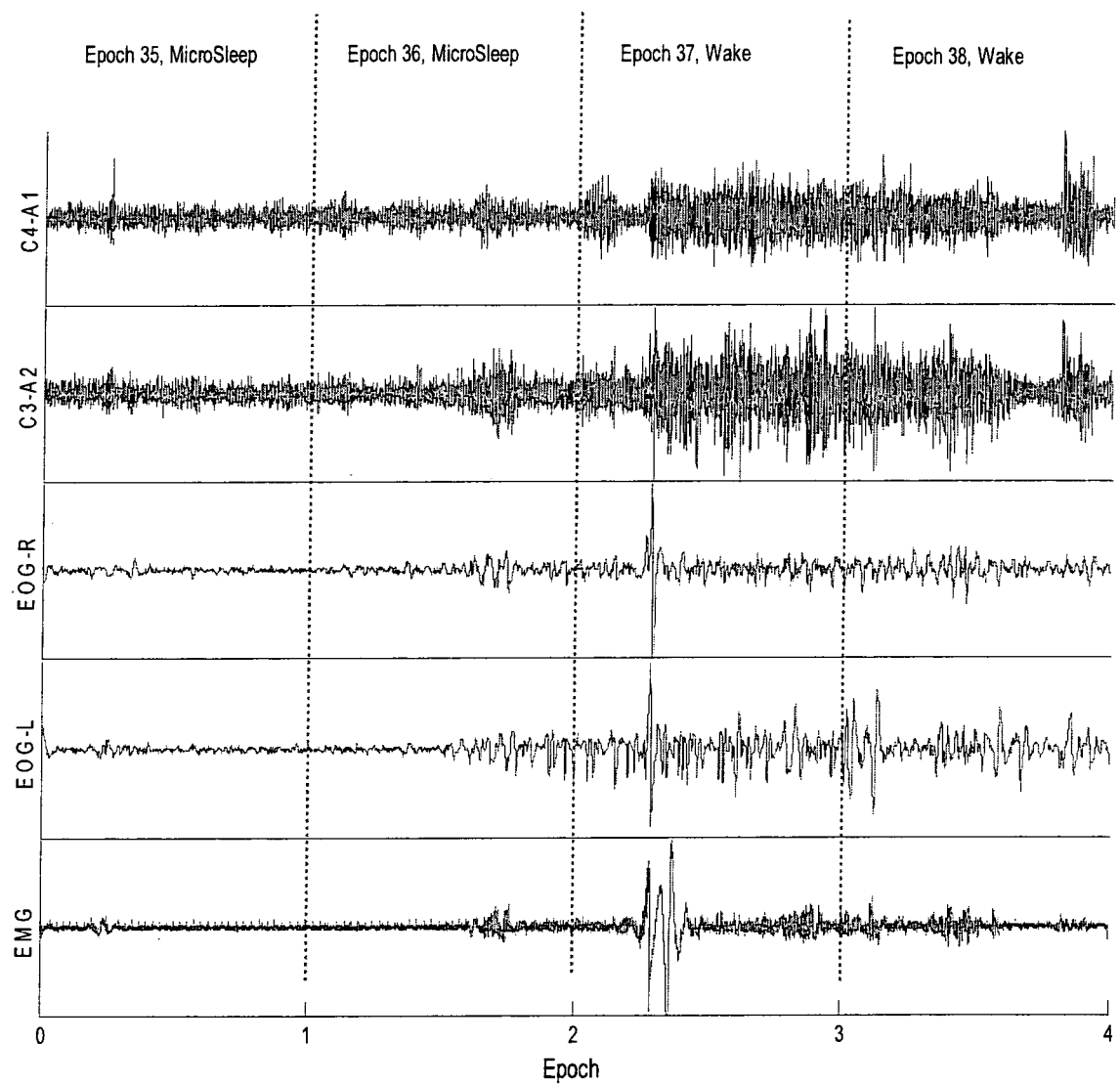
FIG. 16 is a graph of physiological parameters of the subject recorded over a brief time interval of the graph of FIG. 15.

Finally, it is of great interest to explore how the micro-sleep events defined via $\xi_{20}$ correspond with micro-sleep defined by the AASM. As an illustration, in FIG. 16 we show the EEG (C4-A1, C3-A2), EOG (left and right eye) and EMG data from the epochs 35, 36, 37, and 38 as marked on FIG. 15(*a*). Epochs 35 and 36 of FIG. 16 clearly follow the micro-sleep characteristics as defined by AASM, whereas epochs 37 and 38 do not. The micro-sleep defined by AASM agrees with the micro-sleep events defined via $\xi_{20}$ according to the preferred embodiment of the present invention.

The SI index that has been described can be used to identify the level of sleepiness of an individual, on a real-time basis. This is expected to contribute significantly to the monitoring of sleepiness of truck drivers etc. with a view towards timely intervention to prevent events of micro-sleep/sleep and accidents.

4.1 A Dedicated Sleep Architecture Estimator

Figure 19:
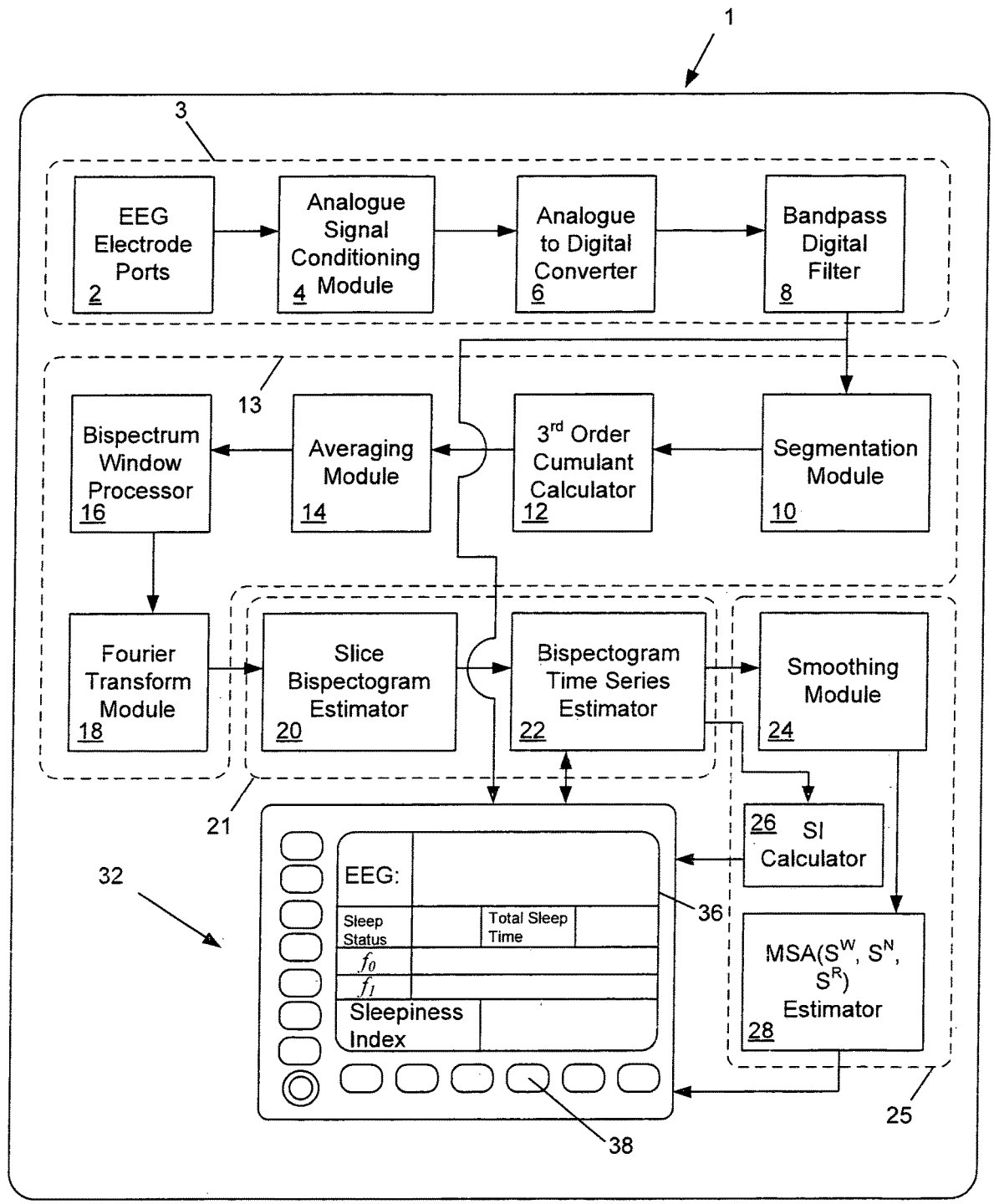
FIG. 19 is a block diagram of an apparatus for detecting and indicating sleep states according to an embodiment of the present invention.

Referring now to FIG. 19 there is depicted a block diagram of a Sleep Architecture Estimator 1 according to an embodiment of the present invention. The following embodiment makes use of circuit blocks that are arranged to analyse bispectra, however as previously discussed, other higher order spectra might also be used such as the trispectrum. It will be realised that the blocks that are depicted are provided as separate interconnected circuit modules, as shown. Alternatively in another embodiment they may be implemented as virtual modules by a machine such as a suitably programmed high speed computer, preferably including one or more dedicated digital signal processing integrated circuits. In the latter alternative an aspect of the invention encompasses a program storage device, for example an optical or magnetic disk or memory circuit. The program storage device is readable by the machine and tangibly embodies a program of instructions executable by the machine to cause the machine to perform a method according to the present invention, for example preferably the method described above in sections 2. and 3. The computer preferably includes a suitable analog to digital converter with ports to receive EEG electrodes for monitoring a subject. The computer also includes a graphical display for displaying classifications of sleep that are determined during execution of the program for viewing by a human operator. A keyboard and mouse are also included in order that the operator can vary parameters of the program, such as thresholds for example.

The Sleep Architecture Estimator 1 includes ports for connection of EEG electrodes 2. The ports are connected to an analogue signal conditioning module 2, which contains circuitry receiving and conditioning the EEG signals. This circuitry typically includes AC coupling to high input impedance differential amplifiers, noise filtering and limiting. The conditioned analogue signal is passed to an analogue to digital converter module 6 which includes an antialising filter. The digital signal from ADC 6 is passed to a bandpass digital filter 8 to remove out-of-band noise, including mains power distribution frequency hum.

Modules 2 to 8, as described above may collectively be referred to as an EEG digital signal assembly 3, for converting analogue EEG signals into digital EEG signals.

A Segmentation Module 10 is coupled to the output of the bandpass digital filter 8 in order to receive the filtered digital signal. Segmentation Module 10 is arranged to segment the filtered digital signal from the bandpass digital filter 8 into a number of records, each comprising a plurality of samples. The Segmentation Module 10 is further arranged to subtract the mean of each record to form a digital signal representing zero-mean sub-segments. A $3^{rd}$ Order Cumulant Calculator 12 is coupled to the output of segmentation module 10. The Cumulant Calculator 12 is arranged to produce a signal representing an estimate of the $3^{rd}$ order cumulants of each sub-segment. An Averaging Module 14 receives the $3^{rd}$ order cumulant signal and processes it to produce an overall cumulant estimate signal.

A Bispectrum Window Processor 16 receives the overall cumulant estimate signal and is arranged to produce a windowed cumulant signal in accordance with a minimum bispectrum-bias supremum window.

The output of the Bispectrum Window Processor 16 is coupled to a 2-D Fourier Transform Module 18, which is arranged to process the windowed cumulant signal in order to produce a bispectrum signal that represents an estimate of the bispectrum of the corresponding segment.

Modules 10 to 18, as described above, may collectively be referred to as a bispectrum assembly 13 to convert the digital EEG signals from bandpass digital filter 8 into signals representing bispectrum values.

In an alternative embodiment the bispectrum assembly is arranged to directly determine the bispectrum estimate according to equation (8A) as previously described. According to the direct calculation embodiment of the invention the Cumulant Calculator 12 is not required. Direct method estimation is computationally much less expensive, but has somewhat higher estimation variance (leading to poorer performance).

A Slice Bispectogram Estimator 20 receives the output from the Fourier Transform Module 18 and is arranged process the bi-spectrum signal to calculate values for a slice of the bispectrum. As previously described, the particular slice of the bispectrum that is favoured is the line described by $\omega_1=\omega_2$ in the $(\omega_1,\omega_2)$-plane. The Slice Bispectogram Estimator calculates the values for the slice and generates a representative digital signal that is output to the Bispectogram Time Series Estimator 22.

The Bispectrum Time Series Estimator 22 is arranged to process the output from the Slice Bispectogram Estimator in order to produce two Bispectrum Time Series data signals at first and second frequencies $f_0$ and $f_1$. These two frequencies are preferably set at 2 Hz and 20 Hz respectively although they may be user adjusted within limits.

Modules 20 and 22 may be collectively referred to as a bispectrum time series assembly 21 for generating bispectrum time series at the first and second frequencies.

A pre-processing module 24 receives the output from the Bispectogram Estimator and is arranged to operate on the 2 Hz time series data signal to apply smoothing, de-trending and histogram equalization.

The pre-processed 2 Hz time series data signal, and the 20 Hz time series data signal, are passed to an MSA estimator module 28. The MSA estimator is arranged to processes the time series data signals and includes comparators to compare them to predetermined threshold values as described in steps T1, T2 and T3 of section 3.1 E above. On the basis of those comparisons the MSA Estimator 28 produces a sleep state signal that indicates any one of Waking, Non-REM and REM sleep states. The sleep state signal is passed to a User Interface 32, as will be discussed further below. In another embodiment of the invention further modules may be incorporated to provided a method of diagnosing obstructive sleep based on the determined macro sleep states.

A Sleepiness index Calculator 26 processes the 20 Hz time series data signal from the Bispectogram Time Series Estimator 22. The Sleepiness Index Calculator 26 is arranged to determine the fraction of the time that the magnitude of the 20 Hz time, in each segment, that the series data signal maintains a value approaching zero (i.e. at or less than ($s_o$) as discussed in section 3.4 above).

Modules 24 to 28 may be collectively referred to as a macro-sleep architecture assembly 25 for producing classification signals indicating classification of segments of the EEG signals into macro-sleep states such as Sleep, Wake and NREM sleep and REM sleep.

A User Interface 32 is provided which communicates with the MSA Estimator module 28, the Sleepiness Index Calculator 26, the Bandpass Digital Filter 8 and the Bispectogram Time Series Estimator 22. The User Interface 32 includes a visual display 36 to display information to a user such as the EEG waveform, sleep state, total sleep time, current $f_0$ and $f_1$ values and current sleepiness index value. Operator buttons 38 are disposed about the screen to allow an operator to enter control parameters via an interactive menu system which is displayed upon the screen in use.

Figure 20:
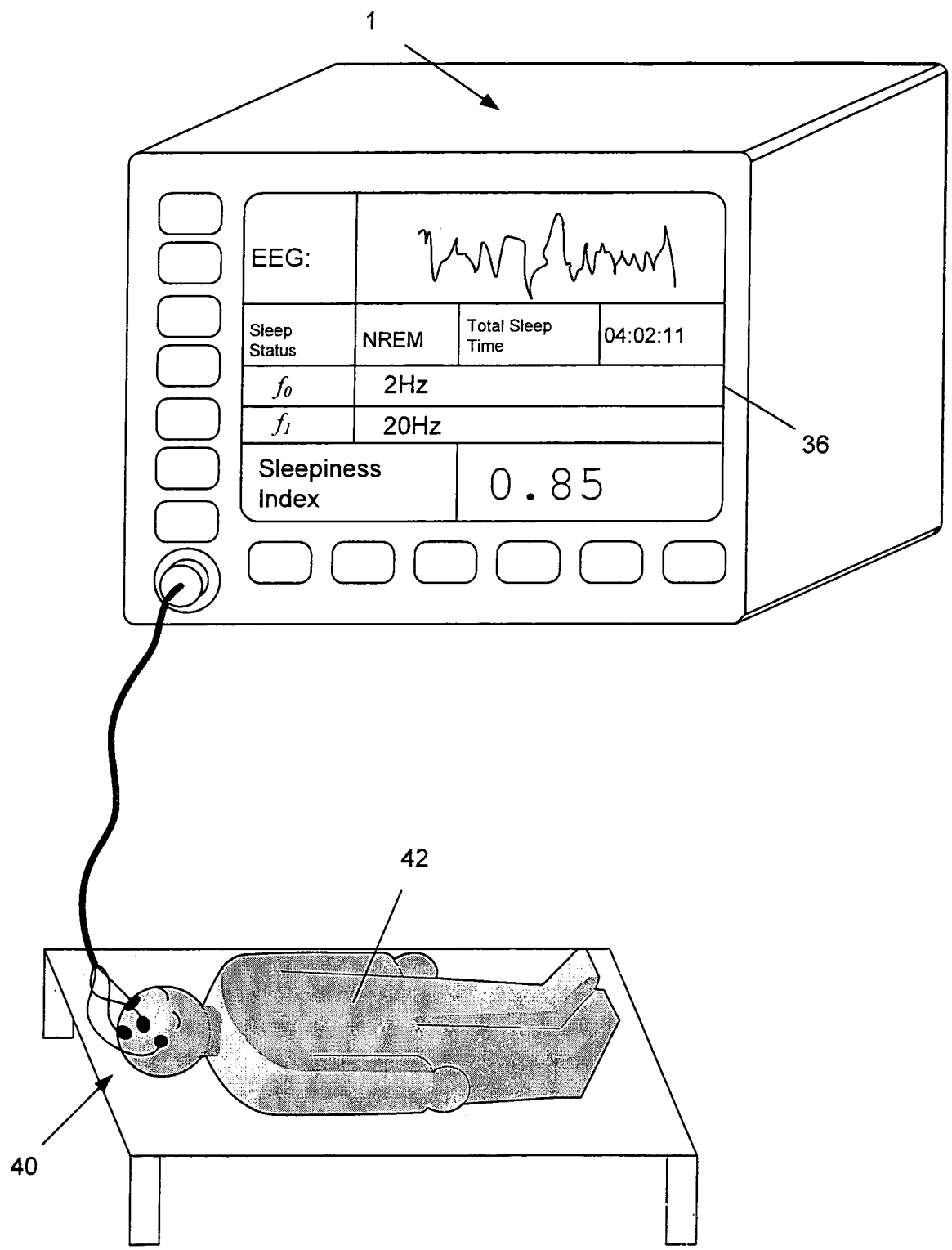
FIG. 20 is a diagram showing the apparatus of FIG. 19 in use.

FIG. 20 shows the Sleep Architecture Estimator in use connected, via electrodes 40 to a patient 42 with display 36 showing the patient's EEG signal and particular information in regard to the patient's sleep state.

The Sleepiness Index may be used for in-facility MSLT and MWT tests, i.e. automated, objective estimation of sleep onset, sleep latencies etc, using just one EEG channel. Furthermore, the described apparatus may be used to automatically score macro sleep states in overnight PSG tests.

4.2 A Driver Sleepiness Monitoring System

Figure 21:
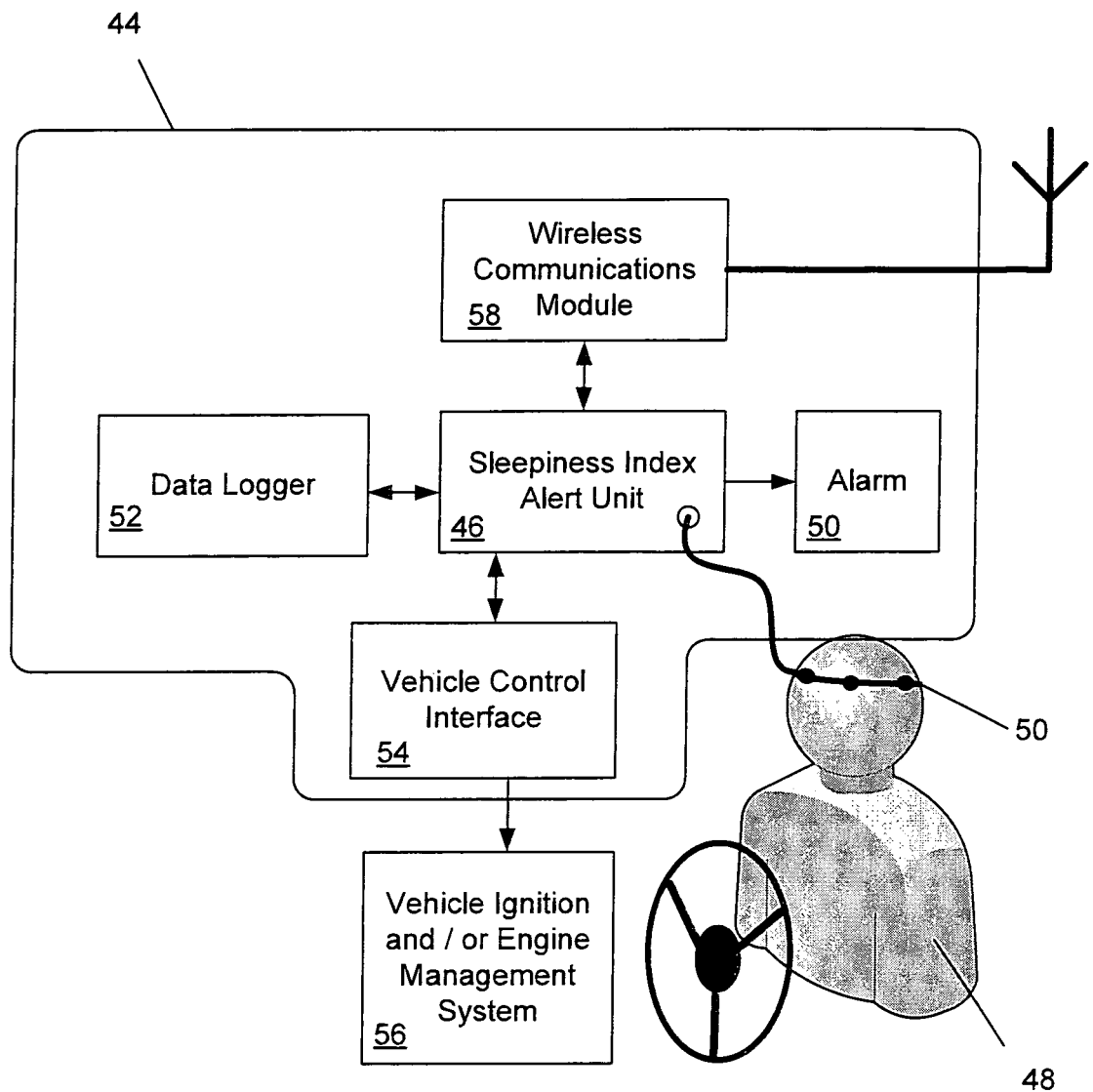
FIG. 21 is a block diagram of an apparatus for detecting sleepiness of a subject in a vehicle according to a further embodiment of the present invention.

Referring now to FIG. 21, there is depicted a block diagram of a Driver Sleepiness Monitoring System 44, according to an embodiment of the present invention in use.

The sleepiness monitoring system includes a Sleepiness Index Alert Unit 46 which incorporates modules 2 to 22 and 26 of the Sleep Architecture Estimator 1 of FIG. 19. The Sleepiness Index Alert Unit 46 receives EEG signals from driver 48 via a headband mounted set of electrodes 50 and in responses produces an ongoing sleepiness index. Although a cable connection is shown to the set of electrodes 50, a wireless connection may be used instead.

In the event of the sleepiness index rising above a predetermined threshold for longer than a minimum time frame, or more than a minimum number of times in a predetermined time period, then the Sleepiness Index Alert Unit 46 is arranged to activate alarm 50, which requires manual switch-off by the driver within a specified time period, in order to increase the wakefulness of driver 48.

In the event of the sleepiness index falling below a predetermined threshold for longer than a minimum time frame, or more than a minimum number of times in a predetermined time period, then the Sleepiness Index Alert Unit 46 is arranged to activate the driver intervention module (eg. alarm) 50 in order to increase the wakefulness of driver 48.

The Sleepiness Index Alert Unit 46 also communicates with a Vehicle Control Interface 54 that in turn is arranged to control the vehicle's engine via the engine management system 56.

A data logger 52 is provided, that is coupled to the Sleepiness Index Alert Unit 46 and which is arranged to record EEG and sleepiness index data of the driver 48. A wireless communications module 58, capable of communicating with a home base via a cellular phone network, is coupled to the Sleepiness Index Alert Unit. Consequently the Sleepiness Index Alert Unit 46 is able to send and receive data relating to the driver's state of wakefulness to the home base. This information may be used to organise a replacement driver for example.

The Driver Sleepiness Monitoring System 44 may also be equipped with a biofeedback assembly containing an audio stimulus source, e.g. MP3 recordings or radio receiver, to provide stimulus such as music, sports commentaries, etc. to the driver in order to lower the driver's sleepiness index. A continual display of the sleepiness index may also be displayed to the driver including prompts, for example requests for the Driver to stop for a cup of coffee, upon the sleepiness index climbing above a predetermined threshold.

5. Conclusion

A method and apparatus for estimating Macro Sleep Architecture (MSA) and Sleepiness Index (SI) as the indicator of sleepiness, using single channel of EEG data, has been described.

The inventors' intensive statistical analysis of the 20,714 epochs from 23 subjects showed a significant agreement between the proposed Higher-Order-Spectra Based technique (HESS) and Technician Scored Sleep States (TSSS). On an average there was an agreement of 77.63% (±9.9%) between TSSS and HESS in classifying sleep into three macro sleep states, State Wake ($S^W$), State REM ($S^R$) and State NREM ($S^N$). This level of agreement is considered an excellent result in clinical sleep scoring, observing that it is on a par with intra-scorer agreement [12] of expert human technologists. Note that the agreement reported on the HESS technique was computed on subjects spanning a large range of RDI, whereas the intra-scorer agreement of humans deteriorates further in the presence of OSAHS cases [13]. In addition, the HESS requires only one channel of EEG, whereas the TSSS uses multiple modes of signals.

The MSA parameters such as NREM/REM stages, Total Sleep Time, Sleep efficiency and REM sleep latency were computed by HESS with significantly high accuracy and correlation, using fully automated algorithms. These are the most important EEG-based parameters resulting from a PSG test. Our ability to compute the parameters reliably, objectively and using a single channel of EEG should make a dramatic impact on the diagnosis and treatment of OSAHS as well a range of other sleep disease such as insomnia.

MSLT and MWT are the main measures of sleepiness used in the clinical environment. They are, however, complicated tests requiring access to sleep laboratories and the services of experienced sleep technologists. Even then, the computation of parameters such as the SL and Sleep Onset are fraught with subjective elements. The Sleepiness Index provides an elegant solution to these problems. It can be automatically computed from a single channel of EEG data at real-time.

SI index is reliable and it is expected that it can be also used as a tool to monitor the sleepiness of humans in hazardous environments such as driving or operating mining equipment.

Appendix A

In Appendix A we provide the standard definitions of Apnea, Hypopnea and Arousals as formulated by professional sleep disorders organizations such as the AASM [9] and ASDA [33]. These definitions are routinely used by sleep physicians around the world to diagnose and treat OSAHS.

Definition of Apnea (AASM):
  Cessation of airflow ≥10 s (with oxygen desaturation undefined) OR
  Cessation of airflow <10 s (but at least one respiratory cycle) with oxygen desaturation ≥3%.
  These events can occur with or without arousal Definition of Hypopnea (AASM): an event to be defined as hypopnea it should fulfil criterion (a) or (b), plus (c) of the following:
  (a) A clear decrease (≥50%) in amplitude from base line of a valid measure of breathing during sleep. Baseline is defined as the mean amplitude of stable breathing or the mean of three largest breaths in the two minutes preceding onset of the event.
  (b) A clear amplitude reduction but does not reach criteria (a) but is associated with oxygen de-saturation >3% or an arousal.
  (c) Event lasts ≥10 seconds.

Definition of Arousals (ASDA) [33]: American Sleep Disorder Association defines EEG arousals (EEGA) as abrupt shift in EEG frequency, which may include theta, alpha activity and/or frequencies greater than 16 Hz (but not sleep spindles) subjected to following scoring rules:
  the subject must be asleep for a minimum period of 10 s before declaring an Arousal event,
  EEG frequency shift must be sustained for a 3 s duration or more, and,
  EEG arousal from REM sleep requires presence of simultaneous increase in the sub mental EMG amplitude.

Appendix B [10]

Respiratory Disturbance Index (RDI) is defined as the average number of apnea/hypopnea events per hour of sleep.

Arousal Index (ArI) is defined as the average number of arousal events per hour of sleep.

Total time in Bed (TTB) is the time spent on the bed from the 'lights off' when the recording starts in the night to the 'lights on' in the morning when the recoding ends.

Total Sleep Time (TST) is defined as the actual sleep time (total time spend in REM and NREM sleep).

Sleep Efficiency (SE) is defined as the percentage ratio 100×(TST/TTB) %.

REM sleep Latency (RSL) is defined as the time between the sleep on-set and the first occurrence of REM sleep.

Appendix C [6]

Rectschaffen and Kales (R&K) in 1968 [11] laid the rules for manual scoring of sleep stages. These rules are very broad and complex, in here we are just giving a short summary of these rules. R&K rules require EEG, EMG and EOG channels for implementation.

Macro Sleep State Wake ($S^W$): When a person is awake and active, EEG shows high beta activity (frequency >16 Hz) with low voltage. As the person starts relaxing (with eyes closed) and gets drowsy EEG shows abundance of alpha (8-12 Hz) activity. Voluntary random slow eye movements can be seen in EOG. EMG is tonic with relatively high voluntary activity.

Macro Sleep State NREM ($S^N$): after the sleep onset, EEG shows low voltage and mixed frequency activity. Theta (4-7 Hz) activity increases. The NREM state is further subdivided into four stages; in Stage 1 features such as sharp vertex waves appear; EOG shows slow eye movement; EMG activity decreases. In Stage 2, EEG activity is full of features such as spindles and k-complexes; EOG activity disappears; EMG shows very low tonic activity. In Stage 3 and Stage 4 EEG shows an abundance of delta activity (high voltage (>75 microV), low-frequency (<3 Hz) waves); no EOG activity and very low tonic EMG activity.

Macro Sleep State REM ($S^R$): EEG shows low voltage mixed frequency (range of high theta and slow alpha) sawtooth wave like activity. EOG shows phasic random eye movement activity. In EMG tonic activity gets suppressed and phasic twitches appears.

Appendix D [6, 34, 35]

Kappa statistic is widely used in situations where the agreement between two techniques should be compared. In Appendix D we provide a guideline for interpreting the Kappa values.

| Kappa | Interpretation [31] |
| --- | --- |
| <0 | Less than chance agreement |
| 0.01-0.20 | Slight agreement |
| 0.21-0.40 | Fair agreement |
| 0.41-0.60 | Moderate agreement |
| 0.61-0.80 | Substantial agreement |
| 0.81-1 | Almost perfect agreement |

Appendix E [6, 28]

Multiple Sleep Latency Test: In MSLT a series of nap opportunities (4-6) are presented to the subject undergoing test at 2 hour intervals beginning approximately 2 hour after morning awakening [6]. Subjects in MSLT test are instructed not to resist themselves from falling sleep. Electrophysiological signals which are recorded to detect sleep onset in MSLT are (i) 4 channel EEGs (C3, C4, O1, O2 with reference to A1 and A2). (ii) left and right eye Electro-oculograms (EOGs), and (iii) submentalis electromyogram (EMG). Each MSLT recording goes for at least 20 minutes. If no sleep onset occurs within 20 minutes than nap opportunity is terminated. If sleep onset occurs before 20 minutes than test session is continued for 15 minutes after sleep onset. Sleep Latency in MSLT is defined as the elapsed time from the start of the test to the first 30-sec epoch scored as sleep. Pathological sleepiness is defined if mean SL is less than or equal to 5 minutes.

Maintenance of Wakefulness Test: The test procedures are similar to MSLT. The only difference is the objective of the test and instructions given to the test subject. The subject is instructed to attempt to remain awake and objective of the test is to assess the function of the underlying wakefulness system.

Appendix F

The method of computing values for the thresholds, $\varepsilon_2$, $\varepsilon_{20}$, $\varepsilon'_{20}$ and D used in the REM combining rule, used in Section 3.1, (E) and section 3.2 respectively will now be described.

Figure 13A:
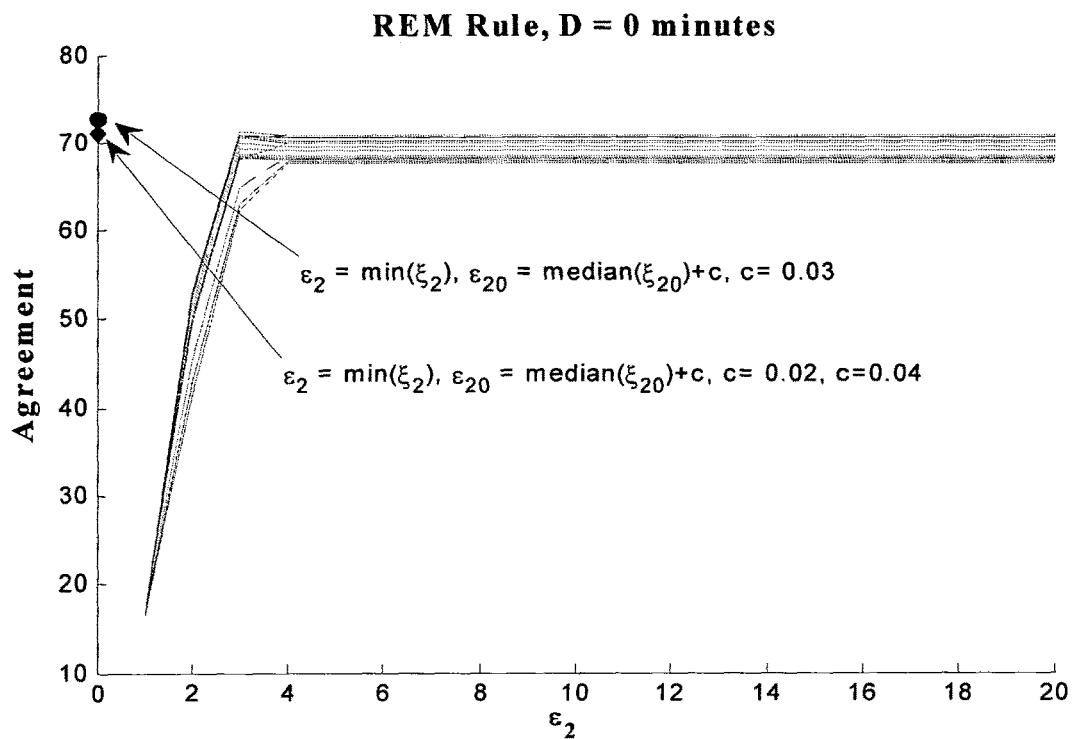
FIG. 13A is a graph illustrating the results of a search for optimum threshold values used in a method according to an embodiment of the present invention.
Figure 13B:
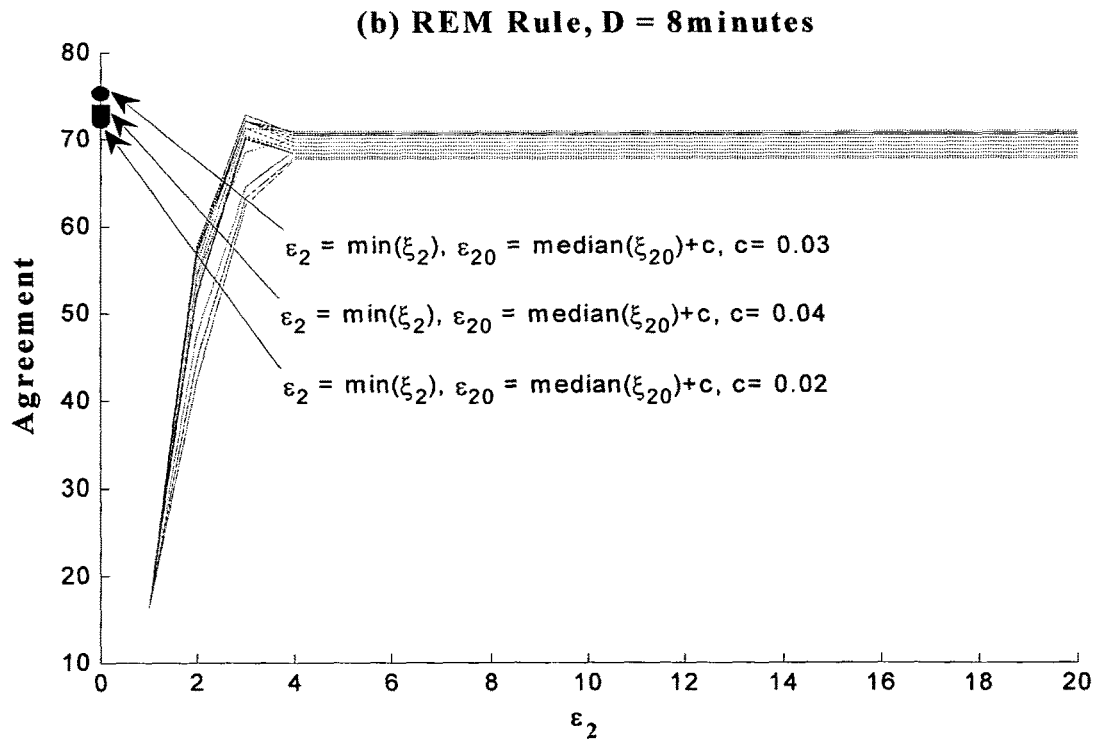
FIG. 13B is a further graph illustrating the results of a search for optimum threshold values used in a method according to an embodiment of the present invention.

(a) Thresholds ($\Delta$), $\varepsilon_2$ and $\varepsilon_{20}$: Values for the thresholds ($\Delta$) $\varepsilon_{20}$ and $\varepsilon_2$ were decided after a careful search process, such that the Agreement between HESS classification (WAKE/NREM/REM) and TSSS was optimized. Initially $\varepsilon_2$ and $\varepsilon_{20}$ were set at high values. Both the thresholds were then decreased consecutively in several steps and $\Delta$ chosen as the combination of $\varepsilon_2$ and $\varepsilon_{20}$, please see (9)-(11). For each combination (300) of thresholds set the agreement between TSSS and HESS was computed in estimating, $S^W$, $S^N$, $S^R$. Those values for $\varepsilon_2$ and $\varepsilon_{20}$ for which agreement was optimised were selected. FIGS. 13A and 13B graphically illustrate the results of this search. From the FIG. 7 it was possible to obtain the absolute values for $\varepsilon_{20}$ and $\varepsilon_2$ at which agreement between HESS and TSSS is optimised. However, it was observed that by using varying threshold (threshold varies for every patient depending on the BTS) such that $\varepsilon_{20}=\text{median}(\xi_{20})+c$ and $\varepsilon_2=\min(\xi'_2)$, the agreement between TSSS and HESS further increases, FIG. 13A, 13B, where 'c' is a constant, whose value was set at 0.03 after a search process. These values of $\Delta$ were used in step (T1) and (T2) of section 3.1. At these values the best overall agreement between TSSS and HESS of 75.17% was achieved. The agreement was 74 and 73 when c=0.02 and 0.04 respectively.

$$\varepsilon_2 \in \{1, 0.67, 0.44, 0.3, 0.20, 0.13, 0.09, 0.058, 0.04, 0.026, 0.017, 0.01, 0.007, 0.005, 0.003, 0.0022, 0.0015, 0.001, 0.00067, 0.0004\} \quad (9)$$

$$\varepsilon_{20} \in \{10, 5, 2.5, 1.25, 0.625, 0.312, 0.156, 0.078, 0.039, 0.019, 0.009, 0.0048, 0.0024, 0.0012, 0.0006\} \quad (10)$$

$$\Delta = \{\varepsilon_2, \varepsilon_{20}\} \quad (11)$$

Figure 8A:
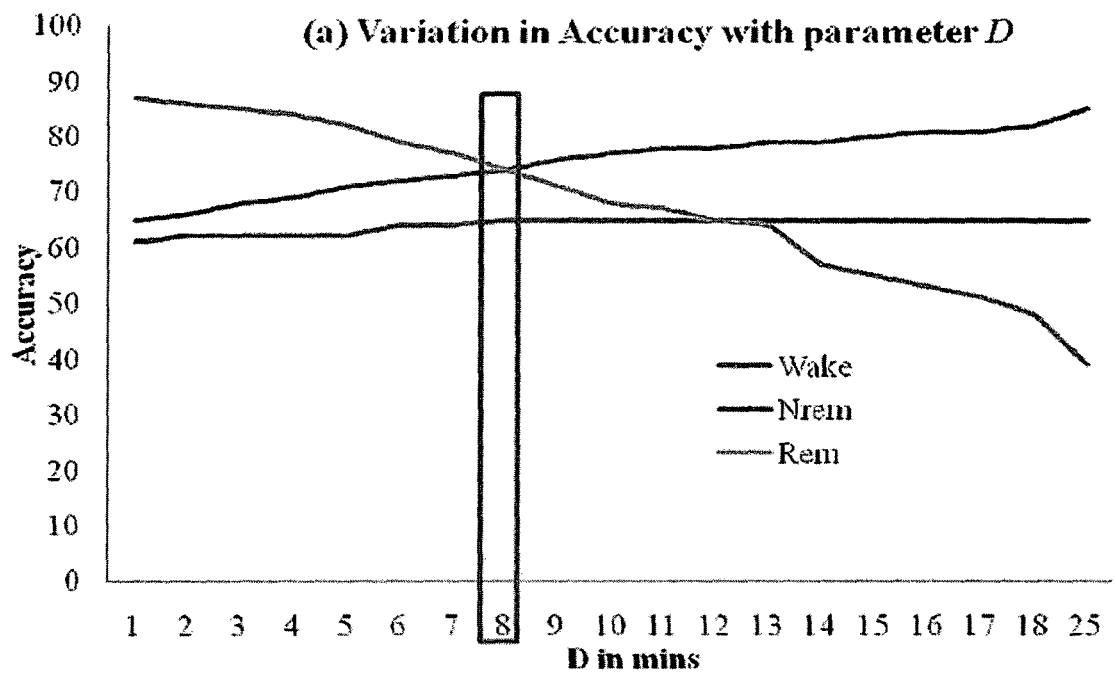
FIG. 8A is a graph illustrating variation in accuracy for each of Wake NREM and REM states as a function of D in minutes.
Figure 8B:
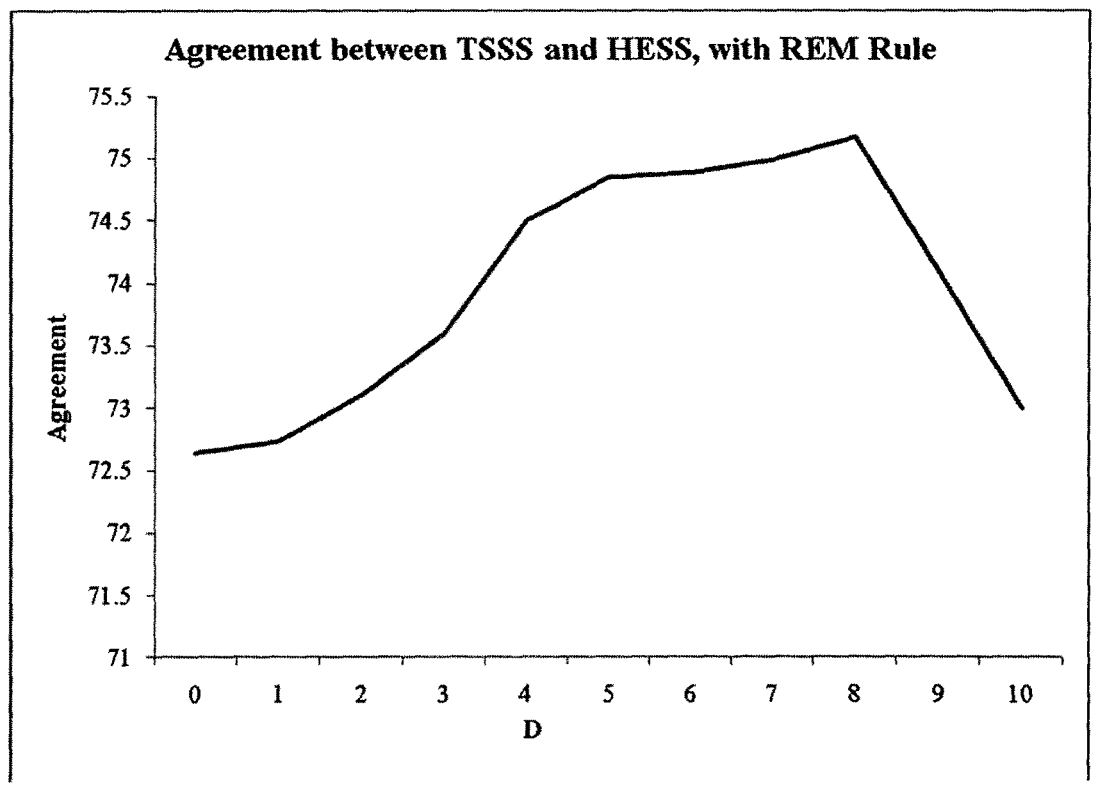
FIG. 8B is a graph showing Agreement value between Technician Scored Sleep States (TSSS) and Higher Orders Statistics based Estimated Sleep States (HESS) for HESS estimates using a REM combining rule varied from D=0 to D=10 minutes.

(b) D for REM-combining Rule and Threshold $\varepsilon'_{20}$: To get the best estimation of D, we varied D from 0 to 10 minutes and applied HESS algorithm on the subjects from the database A. Again D was fixed after a careful search process, at which agreement between TSSS and HESS was optimised. FIG. 8 (AT the end of this document) shows the variation of agreement with D. From the FIG. 8, D=8 min was set. Epochs excluded from the REM sleep state due to REM rule were re-classified into NREM sleep or WAKE state. We used BTS at f=20 Hz for the re-classification as it has shown the excellent ability to distinguish sleep from wake (see FIG. 5). We set the threshold constant at $\varepsilon'_{20}=\text{median}(\xi_{20})$. We checked for the condition $\xi_{20} > \varepsilon'_{20}$. If condition was satisfied then epoch was reclassified as $S^W$ else as $S^N$.

TABLE 1

List of Abbreviations used herein

| | |
|---|---|
| OSAHS | Obstructive Sleep Apnea Hypopnea Syndrome |
| PSG | Polysomnography |
| TTB | Total Time in Bed |
| TST | Total Sleep Time |
| SE | Sleep Efficiency |
| RSL | REM Sleep Latency |
| TSSS | Technician Scored Sleep States |
| HESS | Higher order Estimated Sleep States |
| RDI | Respiratory Risturbance Index |
| AHI | Apnea Hypopnea Index |
| ArI | Arousal Index |
| EEG | Electroencephalogram |
| EOG | Electro-occulogram |
| EMG | Electro-myogram |
| ECG | Electro-cardiogram |
| R&K rules | Rechtschaffen and Kales rules |
| REM | Rapid Eye Movement |
| NREM | Non Rapid Eye Movement |
| HOS | Higher Order Statistics |
| BTS | Bispectogram-Time-Series |
| PPV | Positive Predicted Value |

TABLE 2

List of Symbols used herein

| | |
|---|---|
| $S^W$ | Macro Sleep State "wake" |
| $S^N$ | Macro Sleep State "NREM" |
| $S^R$ | Macro Sleep State "REM" |
| $\omega$ | Discrete Frequency (radians per second) |
| r | Pearson's Correlation Coefficient |
| $\sigma$ | Significance level in statistical tests |
| z | Z statistics in hypothesis test |
| t | t statistic in hypothesis test |
| $\delta$ | Delta frequency range of EEG |
| $\theta$ | Theta frequency range of EEG |
| $\alpha$ | Alpha frequency range of EEG |
| $\beta$ | Beta frequency range of EEG |
| N | Total Number of EEG Epochs |
| $\xi_f$ | Bispectogram Time Series at frequency f |

TABLE 3

Demographic details of the subjects studied.

| Sub. ID | Age | Sex | BMI | RDI |
|---|---|---|---|---|
| (3.1) Database A: Subjects with PSG recordings | | | | |
| 1 | 45 | F | 32.8 | 0.6 |
| 2 | 34 | F | 23.5 | 1.5 |
| 3 | 62 | F | 28.68 | 3.5 |
| 4 | 63 | F | 20.6 | 4.1 |
| 5 | 36 | F | 34.1 | 4.7 |
| 6 | 52 | M | 24.5 | 4.9 |
| 7 | 44 | M | 38.8 | 5.6 |
| 8 | 44 | F | 49.2 | 6.8 |
| 9 | 40 | F | 27.6 | 8.5 |
| 10 | 44 | F | 38.1 | 13.8 |
| 11 | 35 | M | 28.7 | 16.8 |
| 12 | 50 | F | 20.1 | 18.3 |
| 13 | 50 | M | 31.8 | 20.8 |
| 14 | 69 | F | 23.8 | 23.8 |
| 15 | 61 | M | 28.1 | 33.5 |
| 16 | 71 | F | 29.7 | 33.6 |
| 17 | 62 | M | 30.1 | 37.5 |
| 18 | 56 | F | 34.4 | 40.1 |
| 19 | 63 | F | 41.05 | 45.8 |
| 20 | 29 | M | 36.8 | 48.2 |
| 21 | 47 | M | 31.8 | 60.1 |
| 22 | 33 | F | 39.7 | 83.1 |
| 23 | 27 | M | 45.5 | 94.4 |
| (3.2) Database B: Subjects with PSG + Full EEG recording | | | | |
| 24 | 27 | M | 23.7 | 7.1 |
| 25 | 32 | M | 30.2 | 18.5 |

| (3.3) Database C: Subject with MSLT recording | | | | |
|---|---|---|---|---|
| Sub. ID | Age | Sex | BMI | SL |
| 26 | 34 | M | 26.6 | 5.5 |
| 27 | 57 | F | 19.6 | 15.6 |

PSG—Polysomnography, EEG—Electroencephalogram, MSLT—Multiple Sleep Latency Test.

TABLE 4

Variation in Accuracy and PPV value of HESS with change in Threshold, $\varepsilon_2$ and Threshold, $\varepsilon_{20}$ used in the section 3.1 and block diagram of FIG. 7.

| | Min | | | | Min + (μ − min)/2 | | | | μ | | | | μ + (max − μ)/2 | | | | max | | | | |
|---|---|---|---|---|---|---|---|---|---|---|---|---|---|---|---|---|---|---|---|---|---|
| $\varepsilon_2$ | $S^W$ | $S^N$ | $S^R$ | $(S^N + S^R)$ | $S^W$ | $S^N$ | $S^R$ | $(S^N + S^R)$ | $S^W$ | $S^N$ | $S^R$ | $(S^N + S^R)$ | $S^W$ | $S^N$ | $S^R$ | $(S^N + S^R)$ | $S^W$ | $S^N$ | $S^R$ | $(S^N + S^R)$ | $\varepsilon_{20}$ |
| Accuracy | 96 | 10 | 0 | 8 | 96 | 10 | 0 | 8 | 62 | 74 | 74 | 87 | 36 | 74 | 88 | 87 | 28 | 74 | 92 | 87 | Min |
| PPV | 18 | 88 | — | 88 | 18 | 88 | — | 87 | 50 | 88 | 52 | 92 | 59 | 86 | 43 | 71 | 58 | 86 | 40 | 69 | |
| Accuracy | 97 | 8 | 0 | 6 | 97 | 8 | 0 | 7 | 64 | 67 | 77 | 69 | 40 | 67 | 90 | 72 | 32 | 65 | 94 | 71 | {Min + |
| PPV | 17 | 88 | — | 88 | 17 | 88 | — | 88 | 48 | 88 | 45 | 74 | 53 | 87 | 39 | 68 | 51 | 88 | 36 | 66 | (μ − min)/2} |
| Accuracy | 97 | 7 | 0 | 6 | 97 | 7 | 0 | 6 | 65 | 61 | 78 | 64 | 43 | 61 | 90 | 66 | 34 | 58 | 94 | 64 | μ |
| PPV | 17 | 88 | — | 88 | 17 | 88 | — | 88 | 45 | 88 | 41 | 70 | 48 | 87 | 36 | 65 | 46 | 89 | 33 | 61 | |
| Accuracy | 98 | 4 | 0 | 3 | 98 | 4 | — | 3 | 72 | 33 | 61 | 38 | 55 | 30 | 79 | 39 | 48 | 27 | 86 | 38 | {μ + |
| PPV | 17 | 88 | — | 88 | 17 | 88 | — | 88 | 28 | 84 | 31 | 57 | 28 | 86 | 27 | 48 | 27 | 89 | 26 | 45 | (max − μ)/2} |
| Accuracy | 100 | — | — | — | 100 | — | — | — | 100 | — | — | — | 100 | — | — | — | 100 | — | — | — | Max |
| PPV | 17 | — | — | — | 17 | — | — | — | 17 | — | — | — | 17 | — | — | — | 17 | — | — | — | |

In our classification algorithm we used two Bispectrum time series, $\zeta'_2$ and $\zeta_{20}$. $\varepsilon_2$ was computed from $\zeta'_2$ and $\varepsilon_{20}$ from $\zeta_{20}$. To find out the best value for $\varepsilon_2$ and $\varepsilon_{20}$ we varied both and computed accuracy and PPV of HESS. As we can see from the table at $\varepsilon_{20}$ = mean($\zeta_{20}$) and $\varepsilon_2$ = minimum($\zeta'_2$), HESS gives the best results. Min is the Threshold set at the minimum value in the time series, Max is the threshold set at maximum value of time series and mean is the mean value of the time series.

TABLE 5

Contingency table for TSSS vs. HESS sleep states scoring.

| | | | TSSS | | | |
|---|---|---|---|---|---|---|
| | | | Awake | Sleep | | |
| | | | $S^W$ | $S^N$ | $S^R$ | Total |
| HESS | Awake | $S^W$ | 2223 | 1761 | 401 | 4385 |
| | Sleep | $S^N$ | 868 | 10959 | 467 | 12294 |
| | | $S^R$ | 289 | 1341 | 2340 | 3970 |
| | Total | | 3380 | 14061 | 3208 | 20714 |

TABLE 6

Sensitivity and Positive Predicted Value (PPV) of the HESS.

| | $S^W$ | Sleep $(S^N + S^R)$ | $S^N$ | $S^R$ |
|---|---|---|---|---|
| Sensitivity (%) | 65.77 | 87.48 | 77.94 | 72.94 |
| PPV (%) | 50.70 | 92.89 | 89.14 | 58.94 |
| Agreement Between TSSS-HESS | $S^W$ vs $(S^N + S^R)$ | 83.78 | Kappa = 0.48 σ = 0.001, z = 61 | |
| | $S^W$ vs $S^N$ vs $S^R$ | 75.17% | Kappa = 0.54 σ = 0.001, z = 94 | |

The accuracy of the HESS as computed from contingency table is 82.8%.

TABLE 7

Comparison between percentage of $S^W$, $S^N$, $S^R$ sleep computed using TSSS and HESS, across the 23 subjects.

| Sub ID | $S^W$-TSSS | $S^W$-HESS | $S^N$-TSSS | $S^N$-HESS | $S^R$-TSSS | $S^R$-HESS | Agreement | kappa |
|---|---|---|---|---|---|---|---|---|
| 1 | 17 | 15 | 70 | 71 | 13 | 24 | 88 | 0.64 |
| 2 | 7 | 14 | 77 | 76 | 16 | 10 | 81 | 0.61 |
| 3 | 37 | 25 | 59 | 67 | 37 | 26 | 74 | 0.59 |
| 4 | 8 | 7 | 72 | 71 | 20 | 22 | 88 | 0.65 |
| 5 | 14 | 14 | 65 | 60 | 21 | 26 | 81 | 0.66 |
| 6 | 14 | 21 | 67 | 58 | 20 | 21 | 83 | 0.69 |
| 7 | 30 | 24 | 61 | 62 | 9 | 14 | 76 | 0.56 |
| 8 | 13 | 9 | 65 | 53 | 22 | 37 | 76 | 0.44 |
| 9 | 19 | 21 | 65 | 66 | 16 | 13 | 64 | 0.49 |
| 10 | 12 | 16 | 67 | 60 | 21 | 24 | 83 | 0.67 |
| 11 | 10 | 18 | 76 | 65 | 14 | 17 | 80 | 0.57 |
| 12 | 31 | 19 | 58 | 66 | 11 | 15 | 82 | 0.66 |
| 13 | 7 | 12 | 71 | 78 | 22 | 20 | 83 | 0.65 |
| 14 | 27 | 30 | 59 | 63 | 14 | 7 | 82 | 0.68 |
| 15 | 7 | 25 | 85 | 70 | 8 | 5 | 72 | 0.55 |
| 16 | 15 | 17 | 72 | 65 | 13 | 18 | 76 | 0.51 |
| 17 | 19 | 18 | 64 | 38 | 17 | 44 | 61 | 0.48 |
| 18 | 20 | 22 | 66 | 62 | 14 | 16 | 65 | 0.47 |
| 19 | 24 | 26 | 66 | 61 | 10 | 13 | 86 | 0.71 |
| 20 | 16 | 19 | 66 | 63 | 18 | 18 | 75 | 0.65 |
| 21 | 13 | 20 | 75 | 71 | 12 | 9 | 70 | 0.52 |
| 22 | 19 | 21 | 68 | 63 | 13 | 16 | 89 | 0.55 |
| 23 | 9 | 15 | 74 | 58 | 17 | 27 | 71 | 0.43 |

Last two column shows the % agreement and kappa statistic between TSSS and HESS.

TABLE 8

Comparison of estimated sleep states computed using single channel of EEG at different location over the skull with technician scored sleep states.

| | | | Sensitivity | | PPV | | | |
|---|---|---|---|---|---|---|---|---|
| | TST | SE | Sleep | Wake | Sleep | Wake | Agreement | Kappa |
| TSSS | 755 | 73.6 | | | | | | |
| C3 | 739 | 72 | 93 | 86 | 95 | 81 | 87.5 | 0.78 |
| C4 | 750 | 73 | 92 | 87 | 95 | 85.5 | 89.5 | 0.81 |
| Fp1 | 792 | 77.2 | 86.6 | 49.5 | 82.7 | 57.3 | 75.2 | 0.56 |
| Fp2 | 792 | 77.2 | 87.4 | 51.3 | 83.3 | 59.4 | 76.4 | 0.58 |
| F3 | 741 | 72.2 | 89.7 | 76 | 91.4 | 72.6 | 84.5 | 0.73 |
| F4 | 778 | 75.8 | 93 | 72 | 90.3 | 78.7 | 84 | 0.71 |
| Fz | 770 | 75 | 94.2 | 78.2 | 92.3 | 82.8 | 87.2 | 0.78 |
| Cz | 782 | 76.2 | 86.9 | 53.5 | 83.9 | 59.4 | 69.4 | 0.44 |
| T3 | 875 | 85.3 | 95 | 41.7 | 82 | 74.8 | 64.6 | 0.41 |
| T4 | 838 | 81.7 | 95.5 | 56.8 | 86 | 82 | 82 | 0.68 |
| P3 | 755 | 73.6 | 92.7 | 79.7 | 92.7 | 79.7 | 86.8 | 0.77 |
| P4 | 771 | 75.2 | 94.4 | 78.6 | 92.5 | 83.5 | 84.6 | 0.74 |
| T5 | 816 | 79.5 | 90.9 | 52 | 84 | 67.1 | 55.1 | 0.31 |
| T6 | 860 | 83.8 | 95.2 | 48 | 83.6 | 78.3 | 57 | 0.35 |
| O1 | 789 | 76.9 | 90.7 | 61.6 | 86.8 | 70.5 | 67.2 | 0.47 |
| O2 | 854 | 83.2 | 94.6 | 48.3 | 83.6 | 76.2 | 54.6 | 0.27 |

TST—total sleep time, SE—sleep efficiency, PPV—positive predicted value.

TABLE 9

Comparison of Sleep latency computed from SI, that computed by sleep technician using multiple physiological data.

|  | Nap 1 | Nap 2 | Nap 3 | Nap 4 |
|---|---|---|---|---|
| Subject ID 26 | | | | |
| SL - TSSS | 7 | 4 | 2.5 | 8.5 |
| SL - SI | 5.6 | 4.3 | 1.8 | 6.7 |
| Subject ID 27 | | | | |
| SL - TSSS | 5.5 | 11.5 | 6 | 3 |
| SL - SI | 3.9 | 8.1 | 3.3 | 2.8 |

Sleep latency was computed in minutes.

REFERENCES

1. Young T, et al., *The Occurrence of Sleep-Disordered Breathing among Middle-Aged Adults.* N Engl J Med, 1993. 328(17): p. 1230-1235.
2. Young T, et al., *Estimation of clinically diagnosed proportion of sleep apnea syndrome in middle aged men and women.* Sleep, 1997. 20(9): p. 705-706.
3. Puvanendran, K. and K. L. Goh, *From snoring to sleep apnea in a Singapore population.* Sleep Res Online, 1999. 2(1): p. 11-14.
4. "Wake up Australia", Access Economics, for the Steering Committee of Sleep Health Australia. Available from the Australian Sleep Association Website, 2005. www.sleep-aus.on.net/wakeup.pdf.
5. Abeyratne, U. R., A. S. Wakwella, and C. Hukins, *Pitch jump probability measures for the analysis of snoring sounds in apnea.* Physiological Measurement, 2005. 26(5): p. 779-798.
6. Kryger, M. H., T. Roth, and W. C. Dement, *Principles and Practice of Sleep Medicine.* 3 ed. 2000: W. B. Saunders. 1336.
7. Australian Sleep Association, Submission to the Parliament of the Commonwealth of Australia. 1999.
8. Ronald, J., et al., *Obstructive Sleep Apnea Patients Use More Health Care Resources Ten Years Prior to Diagnosis.* Sleep Research Online, 1998. 1(1): p. 71-74.
9. Kushida, C., et al., *Practice parameters for the indications for polysomnography and related procedures.* Polysomnography Task Force, American Sleep Disorders Association Standards of Practice Committee. SLEEP, 1997. 6(20): p. 406-422.
10. Niedermeyer, E. and F. L. d. Silva, *Electroencephalography: Basic principles, clinical applications, and related fields.* 5 ed. 2005: Lippincott Williams & Wilkins. 1309.
11. Rechtschaffen, A. and A. Kales, *A manual of standardized terminology and scoring system for sleep stages of human subjects.* Brain Information Service/Brain Research Institute University of California at Los Angles, 1968 (204).
12. Collop N A, *Scoring variability between polysomnography technologists in different sleep laboratories.* Sleep medicine, 2002. 3(1): p. 43-47.
13. Danker H, et al., *Interrater reliability between scorers from eight European sleep laboratories in subjects with different sleep disorders.* Journal of Sleep Research, 2004. 13: p. 63-69.
14. Suzuki M, et al., *Discrepancy in polysomnography scoring for a patient with obstructive sleep apnea hypopnea syndrome.* he Tohoku journal of experimental medicine, 2005. 206(4): p. 353-360.
15. Whitney C W, Gottlieb D J, and E. al, *Reliability of scoring respiratory disturbance indices and sleep staging.* Sleep, 1998. 21(7): p. 749-757.
16. Robert G N, et al., *Interobserver Agreement Among Sleep Scorers From Different Centers in a Large Dataset.* Sleep, 2000. 23(7).
17. B. Kemp, et al., *A model-based monitor of human sleep stages.* Biological Cybernetics, 1987. 57(6).
18. B. Kim, K. P., *Automatic sleep stage scoring system using genetic algorithms and neural network.* Engineering in Medicine and Biology Society, Proceedings of the 22nd Annual International Conference of the IEEE, 2000. 2: p. 849-850.
19. Djordje P, et al., *Accuracy of Automated Sleep Staging Using Signals from a Single Forehead Site.*
20. M. Qianli, et al., *Sleep-stage Characterization by Nonlinear EEG Analysis using Wavelet-based Multifractal Formalism.* Engineering in Medicine and Biology Society, Proceedings of the 27th Annual International Conference of the IEEE, 2005: p. 4526-4529.
21. O. Pacheco and F. Vaz, *Integrated system for analysis and automatic classification of sleep EEG.* Engineering in Medicine and Biology Society, Proceedings of the 20th Annual International Conference of the IEEE, 1998. 4: p. 2062-2065.
22. Van Hese P, Philips W, and et al, *Automatic Detection of Sleep Stages using EEG.* 23rd Annual Conference—IEEE/EMBS Oct. 25-28, 2001, Istanbul, TURKEY, 2001. 2: p. 1944-1947.
23. Chervin R D, Burns J W, and R. D L, *Electroencephalographic Changes during Respiratory Cycles Predict Sleepiness in Sleep Apnea.* Am. J. Respir. Crit. Care Med., 2005. 171(6): p. 652-658.
24. Dingli, K., et al., *Electroencephalographic spectral analysis: detection of cortical activity changes in sleep apnoea patients.* European Respiratory Journal, 2002. 20(5): p. 1246-1253.
25. V. Svetnik, J. Ma, and e. al., *Evaluation of automated and semi-automated scoring of polysomnographic recordings from a clinical trial using zolpidem in the treatment of insomnia.* Sleep, 2007. 30(11).
26. American Sleep Disorders Association and D.C.S. Committee, *International Classification of Sleep Disorders: Diagnostic and Coding Manual.* American Academy of Sleep Medicine, 2005.
27. Klink, M. and S. F. Quan, *Prevalence of reported sleep disturbances in a general adult population and their relationship to obstructive airways diseases.* Chest, 1987. 91(4): p. 540-546.
28. CARSKADON M A, et al., *Guidelines for the multiple sleep latency test (MSLT): a standard measure of sleepiness.* Sleep, 1986. 9(4): p. 519-524.
29. Mendel, J. M., *Tutorial on higher-order statistics (spectra) in signal processing and system theory: theoretical results and some applications.* Proceedings of IEEE, 1991. 79(3): p. 278-305.
30. Abeyratne, U. R., *Blind reconstruction of non-minimum-phase systems from 1-D oblique slices of bispectrum.* Vision, Image and Signal Processing, IEE Proceedings, 1999. 146(5): p. 253-264.
31. Loader, C., *Smoothing: Local Regression Techniques.* Handbook of Computational Statistics, 2004.
32. Loader, W. S. C. a. C., *Smoothing by Local Regression: Principle and Methods.*
33. Michael Bonnet, D. C., Mary Carskadon (Consultant), Paul Easton (Consultant), Christian Guilleminault (Chairman), Ronald Harper, Boyd Hayes, Max Hirshkowitz, Periklis Ktonas, Sharon Keenan, Mark Pressman (Consultant), Timothy Roehrs, Jack Smith, Jim Walsh, Steven Weber, Philip Westbrook, *ASDA Report EEG Arousals: Scoring Rules And Examples: A Preliminary Report From The Sleep Disorders Atlas Task Force Of The American Sleep Disorders Association*. Sleep, 1992. 2(15): p. 173-184.
34. Feinstein A R and Cicchetti D V, *High agreement but low kappa: I. The problems of two paradoxes*. Journal of Clinical Epidemiology, 1990. 43(6): p. 543-549.
35. Feinstein A R and Cicchetti D V, *High agreement but low kappa: II. The problems of two paradoxes*. Journal of Clinical Epidemiology, 1990. 43(6): p. 551-558.

In compliance with the statute, the invention has been described in language more or less specific to structural or methodical features. The term "comprises" and its variations, such as "comprising" and "comprised of" is used throughout in an inclusive sense and not to the exclusion of any additional features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

The invention claimed is:

1. A method of processing an electroencephalogram (EEG) signal of a subject to determine Waking and Sleep states of the subject, the Sleep state comprising non-rapid eye movement (NREM) sleep and rapid eye movement (REM) sleep states, the method comprising:
    obtaining the EEG signal from EEG electrodes applied to the subject;
    electronically processing the EEG signal to generate a spectrum of third or higher order of the EEG signal;
    electronically processing the spectrum to produce a first spectrum slice time series at a first frequency and a second spectrum slice time series at a second frequency, the first frequency being higher than the second frequency, the first frequency having been selected for discriminating between the Waking and Sleep states, and the second frequency having been selected for discriminating between the NREM sleep and the REM sleep states;
    electronically processing the first spectrum slice time series and the second spectrum slice time series for compliance with predetermined criteria to produce a sleep state signal indicating segments of the EEG signal as being classified as corresponding to either Wake or NREM sleep or REM sleep states of the subject;
    wherein said processing for compliance with predetermined criteria to produce the sleep state signal comprises:
    calculating a median value of the first spectrum slice time series at the first frequency to determine a first threshold value,
    calculating a minimum value of the second spectrum slice time series to determine a second threshold value,
    for each of the segments of the EEG signal:
        if the first spectrum slice time series for the first frequency has a value greater than or equal to the first threshold value, then tangibly classifying the segment as the Waking state,
        or otherwise,
            if the second spectrum slice time series for the second frequency has a value greater than or equal to the second threshold value, then tangibly classifying the segment as the NREM sleep state,
            or otherwise,
                tangibly classify the segment as the REM sleep state; and
    causing the classification(s) to be output to a visual display.

2. A method according to claim 1, wherein the spectrum comprises a bispectrum and the spectrum slice time series each comprise a respective bispectrum slice time series.

3. A method according to claim 2, wherein the second frequency is less than or equal to 2 Hz and the first frequency is greater than or equal to 18 Hz and less than or equal to 23 Hz.

4. A method according to claim 3, further comprising electronically smoothing the second spectrum slice time series prior to processing said second spectrum slice time series signal for compliance with predetermined criteria.

5. A method according to claim 1, further comprising operating an alarm in response to tangibly classifying a segment of the EEG of the subject as the Sleep state.

6. A method according to claim 1, wherein electronically processing the EEG signal to generate a spectrum of third or higher order of the EEG signal comprises an indirect estimation method.

7. A method according to claim 6, wherein the indirect method includes applying a Fourier transform to cumulant values corresponding to the EEG signal.

8. A method according to claim 1, wherein the EEG signal is electronically processed to create a bispectrum signal via a direct estimation method.

9. A method according to claim 1, further comprising electronically processing a signal corresponding to the first spectrum slice time series to produce an index indicating sleepiness of the subject.

10. A method according to claim 9, wherein the index is produced by electronically processing a signal corresponding to a first bispectrum time series, including determining a fraction of time over a predetermined period that said first bispectrum time series approaches a predetermined threshold value.

11. A non-transitory media readable by machine, tangibly embodying a program of non-transitory instructions executable by the machine to cause the machine to perform the method of claim 1 to determine sleep states from the EEG of the subject.

* * * * *